United States Patent
Agrawal et al.

(10) Patent No.: US 10,639,185 B2
(45) Date of Patent: May 5, 2020

(54) SPINAL TREATMENT DEVICES, METHODS, AND SYSTEMS

(71) Applicant: The Trustees of Columbia University in the City of New York, New York, NY (US)

(72) Inventors: Sunil K. Agrawal, Newark, DE (US); Joon-Hyuk Park, Newark, DE (US); Paul Stegall, Kansas City, MO (US)

(73) Assignee: The Trustees of Columbia University in the City of New York, New York, NY (US)

( * ) Notice: Subject to any disclaimer, the term of this patent is extended or adjusted under 35 U.S.C. 154(b) by 700 days.

(21) Appl. No.: 15/306,306

(22) PCT Filed: Apr. 24, 2015

(86) PCT No.: PCT/US2015/027634
§ 371 (c)(1),
(2) Date: Oct. 24, 2016

(87) PCT Pub. No.: WO2015/164814
PCT Pub. Date: Oct. 29, 2015

(65) Prior Publication Data
US 2017/0042717 A1    Feb. 16, 2017

Related U.S. Application Data

(60) Provisional application No. 61/984,547, filed on Apr. 25, 2014, provisional application No. 62/067,569, filed on Oct. 23, 2014.

(51) Int. Cl.
*A61F 5/02* (2006.01)
*A61H 1/02* (2006.01)
*A61B 17/70* (2006.01)

(52) U.S. Cl.
CPC .............. *A61F 5/024* (2013.01); *A61B 17/70* (2013.01); *A61H 1/0292* (2013.01);
(Continued)

(58) Field of Classification Search
CPC .. A61F 5/02; A61F 5/022; A61F 5/024; A61F 5/026; A61F 5/028; A61H 1/0292
(Continued)

(56) References Cited

U.S. PATENT DOCUMENTS 3,358,678 A    12/1967 Kultsar
3,449,769 A    6/1969 Mizen
(Continued)

FOREIGN PATENT DOCUMENTS

KR    20090050917 A    5/2009

OTHER PUBLICATIONS

Awtar S, "Constraint-Based Design of Parallel Kinematic XY Flexure Mechanisms", ASME. J. Mech. Des. 2006;129(8).
(Continued)

*Primary Examiner* — Keri J Nelson
(74) *Attorney, Agent, or Firm* — Potomac Law Group, PLLC; Mark A. Catan

(57) ABSTRACT

Active wearable body brace embodiments provide selectable conformation control of the interface between the trunk of a human subject and the brace, which conformation may be varied over time and responsively to feedback and an updateable prescription. Further active wearable body brace embodiments provide selectable movement control of the interface between the trunk of a human subject and the brace with up to six degrees of freedom between elements to allow a controller to implement operations such as muscle challenges, active support, and passive-like support where actuators mimic springs. Further embodiments may also provide detection functions such as quantifying muscle weakness.
(Continued)

The features of these embodiments may be combined in various ways to provide still further embodiments.

23 Claims, 13 Drawing Sheets

(52) U.S. Cl.
CPC .................. *A61H 2201/018* (2013.01); *A61H 2201/1215* (2013.01); *A61H 2201/1238* (2013.01); *A61H 2201/1246* (2013.01); *A61H 2201/149* (2013.01); *A61H 2201/165* (2013.01); *A61H 2201/1619* (2013.01); *A61H 2201/501* (2013.01); *A61H 2201/5061* (2013.01); *A61H 2201/5069* (2013.01); *A61H 2201/5082* (2013.01); *A61H 2201/5097* (2013.01)

(58) Field of Classification Search
USPC ..................................................... 602/18–19
See application file for complete search history.

(56) References Cited

U.S. PATENT DOCUMENTS

| | | | |
|---|---|---|---|
| 5,324,247 | A | 6/1994 | Lepley |
| 5,456,268 | A | 10/1995 | Bonutti |
| 5,702,389 | A | 12/1997 | Taylor et al. |
| 6,592,538 | B1 | 7/2003 | Hotchkiss et al. |
| 7,632,216 | B2 | 12/2009 | Rahman et al. |
| 7,766,850 | B2 | 8/2010 | Simanovsky |
| 8,795,213 | B2 | 8/2014 | Mills |
| 2004/0077982 | A1 | 4/2004 | Reinecke |
| 2005/0113652 | A1 | 5/2005 | Stark et al. |
| 2008/0195010 | A1 | 8/2008 | Lai et al. |
| 2009/0137934 | A1 | 5/2009 | Seon |
| 2011/0230806 | A1 | 9/2011 | Lou et al. |
| 2013/0278436 | A1 | 10/2013 | Ellis |
| 2013/0317400 | A1 | 11/2013 | Ferezy |
| 2014/0039371 | A1 | 2/2014 | Johnson et al. |

OTHER PUBLICATIONS

Awtar, et al., "An XYZ Parallel-Kinematic Flexure Mechanism With Geometrically Decoupled Degrees of Freedom", ASME Journal of Mechanisms and Robotics, Feb. 2013, vol. 5., 7 pages.
Bishop-Moser et al., "Design of soft robotic actuators using fluid-filled fiber-reinforced elastomeric enclosures in parallel combinations", 2012 IEEE/RSJ International Conference on Intelligent Robots and Systems.
Bowen et al., "A Classification of Action Origami as Systems of Spherical Mechanisms", ASME. J. Mech. Des. 2013;135(11).
Bowen et al., "Adolescent idiopathic scoliosis managed by a nighttime bending brace," Orthopedics, Oct. 1, 2001, vol. 24(10), pp. 967-970.
Carlson JM, "Clinical Biomechanics of Orthotic Treatment of Idiopathic Scoliosis," Journal of Prosthetics and Orthotics 2003; vol. 15, No. 4S, p. 17.
Carragee et al., "Spinal bracing in adolescent idiopathic scoliosis," The New England Journal of Medicine, Oct. 17, 2013, vol. 369(16), pp. 1558-1560.
Cella et al., "Assessment Center", available at http://www.assessmentcenter.net, Last updated Jun. 21, 2017.
De Mauroy et al., "The Lyon brace," Disability and Rehabilitation: Assistive Technology, Jan. 1, 2008, vol. 3(3), pp. 139-145.
Dong Xu, et al., "Freeform Skeletal Shape Optimization of Compliant Mechanisms", J. Mech. Des 125(2), 253-261 (Jun. 11, 2003) (9 pages).
Extended European Search Report for European Patent Application No. 15782261.0 dated Nov. 3, 2017.
Fattah et al., "On the Design of Cable-Suspended Planar Parallel Robots", J. Mech. Des 127(5), 1021-1028 (Oct. 28, 2004) (8 pages).
Federico et al., "Results of treatment of idiopathic scoliosis with the Charleston bending orthosis", Spine, Sep. 1990, vol. 15, pp. 886-887.
Frank P. Castro, Adolescent idiopathic scoliosis, bracing, and the Hueter-Volkmann principle, The Spine Journal 3 2003, 180-185.
Frecker et al., "Topological Synthesis of Compliant Mechanisms Using Multi-Criteria Optimization", J. Mech. Des 119(2), 238-245 (Jun. 1, 1997) (8 pages).
Hao et al., "Design and Modeling of a Large-Range Modular XYZ Compliant Parallel Manipulator Using Identical Spatial Modules", Journal of Mechanism and Robotics, May 2012, pp. 1-10.
Heary et al., "Bracing for scoliosis," Neurosurgery, Sep. 1, 2008, vol. 63, Suppl. 3, pp. A125-A130 (Abstract only).
Hetrick, J.A., "An Energy Formulation for Parametric Size and Shape Optimization of Compliant Mechanisms", J. Mech. Des 121(2), 229-234 (Jun. 1, 1999) (6 pages).
Hoetmer et al., "Negative Stiffness Building Blocks for Statically Balanced Compliant Mechanisms: Design and Testing", J. Mechanisms Robotics 2(4), 041007 (Sep. 30, 2010) (7 pages).
Hopkins, "Synthesis of multi-degree of freedom, parallel flexure system concepts via Freedom and Constraint Topology (FACT)—Part I: Principles", Precision Engineering, vol. 34, Issue 2, Apr. 2010, pp. 259-270.
International Preliminary Report on Patentability for International Patent Application No. PCT/US2015/027634 dated Nov. 3, 2016.
International Search Report and Written Opinion dated Oct. 6, 2015 for International Application No. PCT/US2015/027634.
J. Pusey, "Design and workspace analysis of a 6-6 cable-suspended parallel robot", Mechanism and Machine Theory, vol. 39, Issue 7, Jul. 2004, pp. 761-778.
Kim et al., "Curve Decomposition Analysis for Fixed-Guided Beams With Application to Statically Balanced Compliant Mechanisms", J. Mechanisms Robotics 4(4), 041009 (Sep. 17, 2012) (9 pages).
Krishnan et al., "A Kinetostatic Formulation for Load-Flow Visualization in Compliant Mechanisms", J. Mechanisms Robotics 5(2), 021007 (Apr. 12, 2013) (9 pages).
Krishnan et al., "A Metric to Evaluate and Synthesize Distributed Compliant Mechanisms", downloaded from http://www.cae.tntech.edu/~scanfield/DRAFT-MD-11-1481-0.pdf on Mar. 8, 2019.
Krishnan et al., "Load-Transmitter Constraint Sets: Part II—A Building Block Based Methodology for the Synthesis of Compliant Mechanisms", ASME 2010 International Design Engineering Technical Conferences and Computers and Information in Engineering Conference, vol. 2: 34th Annual Mechanisms and Robotics Conference, Parts A and BMontreal, Quebec, Canada, Aug. 15-18, 2010.
Krishnan, et al., "An Intrinsic Geometric Framework for the Building Block Synthesis of Single Point Compliant Mechanisms", J. Mechanisms Robotics 3(1), 011001 (Nov. 23, 2010) (9 pages).
Labelle et al., "Three-dimensional Effect of the Boston Brace on the Thoracic Spine and Rib Cage", Spine, Jan. 1, 1996, vol. 21(1), pp. 59-64.
M. Griffis J. Duffy, "A forward displacement analysis of a class of stewart platforms", Journal of Robotic Systems, 1989.
Marco Carricato, "Singularity-Free Fully-Isotropic Translational Parallel Manipulators", The International Journal of Robotics Research, 2002.
Merlet, J. P., "Parallel Robots", Springer 2006.
Miller et al., "Electronic monitoring improves brace-wearing compliance in patients with adolescent idiopathic scoliosis: a randomized clinical trial," Spine, Apr. 20, 2012, vol. 37(9), pp. 717-721.
Negrini et al., "Braces for idiopathic scoliosis in adolescents (Review)," The Cochrane Library, Jun. 18, 2015, Issue 6.
Oh, et al., "Dynamic Modeling and Robust Controller Design of a Two-Stage Parallel Cable Robot", Department of Mechanical Engineering University of Delaware, 6 pages, downloaded from http://citeseerx.ist.psu.edu/viewdoc/download?doi=10.1.1.90.5036&rep=rep1&type=pdf on Feb. 13, 2019.
Olafsson et al., "Does bracing affect self-image? A prospective study on 54 patients with adolescent idiopathic scoliosis," European Spine Journal, Oct. 1, 1999, vol. 8(5), pp. 402-405.

(56) References Cited

OTHER PUBLICATIONS

P. Lusk, Craig & L. Howell, Larry, "Spherical Bistable Micromechanism", Journal of Mechanical Design—J Mech Design. 130, Apr. 2008.

Pedersen et al., "Topology synthesis of large-displacement compliant mechanisms", International Journal for Numerical Methods in Engineering, vol. 50, Issue 12, Apr. 20, 2001, pp. 2683-2705.

Price et al., "Nighttime bracing for adolescent idiopathic scoliosis with the Charleston bending brace", Preliminary report, Spine, Dec. 1990, vol. 15(12), 1294-1299.

R. Verhoeven, "Workspace, Stiffness, Singularities and Classification of Tendon-Driven Stewart Platforms", Advances in Robot Kinematics: Analysis and Control, 1998.

S. Canfield, et al., "Topology optimization of compliant mechanical amplifiers for piezoelectric actuators", Structural and Multidisciplinary Optimization, Dec. 2000, vol. 20, Issue 4, pp. 269-279.

S. K. Agrawal, "Fabrication and Analysis of a Novel 3 DOF Parallel Wrist Mechanism", J. Mech. Des 117(2A), 343-345 (Jun. 1, 1995) (3 pages).

S. K. Agrawal, "Statics of In-Parallel Manipulator Systems", J. Mech. Des 114(4), 564-568 (Dec. 1, 1992) (5 pages).

S.K. Agrawal, "Workspace boundaries of in-parallel manipulator systems", International Journal of Robotics and Automation, vol. 7, No. 2, 1992, 94-99.

Song et al., "Forward Position Analysis of Nearly General Stewart Platforms", Journal of Mechanical Design, 1994.

Su, Hai-Jun & Tari, Hafez. (2011). On Line Screw Systems and Their Application to Flexure Synthesis. Journal of Mechanisms and Robotics, Feb. 2011, vol. 3.

Trease et al., "Design of Large-Displacement Compliant Joints", ASME Transactions, ASME Journal of Mechanical Design, vol. 127, No. 4, Jul. 2005.

Van Den Hout et al., "Interface corrective force measurements in Boston brace treatment," European Spine Journal, Mar. 1, 2002, vol. 11(4), pp. 332-335.

Watts et al., "The Boston brace system for the treatment of low thoracic and lumbar scoliosis by the use of a girdle without superstructure," Clinical Orthopaedics and Related Research, 1977 (vol. 126, pp. 87-92.

Weiss, "Brace Technology" Thematic Series—the Gensingen brace(TM) in the treatment of scoliosis, Scoliosis, Oct. 13, 2010, vol. 5(1), pp. S-22 (18 pages).

Wilding et al., "Spherical lamina emergent mechanisms", Mechanism and Machine Theory, vol. 49, Mar. 2012, pp. 187-197.

Z. Huang, "Type Synthesis of Symmetrical Lower-Mobility Parallel Mechanisms Using the Constraint-Synthesis Method", The International Journal of Robotics Research 22(1):59-79, Jan. 2003.

Office Action (Communication Pursuant to Article 94(3) EPC) dated May 3, 2019 for European Patent Application No. 15782261.0.

TABLE I: ORIENTATION ERROR

| MIDDLE | $\phi$ (deg) | $\theta$ (deg) | $\psi$ (deg) |
|---|---|---|---|
| THREE POINT | 0.37 ± 0.43 | 0.18 ± 0.12 | 0.23 ± 0.21 |
| FLEXION | 0.07 ± 0.05 | 0.15 ± 0.10 | 0.43 ± 0.27 |
| LATERAL BENDING | 0.14 ± 0.08 | 0.29 ± 0.27 | 0.21 ± 0.16 |
| ROTATION FOLLOW | 0.09 ± 0.08 | 0.15 ± 0.13 | 0.18 ± 0.13 |
| ROTATION MIRROR | 0.07 ± 0.05 | 0.17 ± 0.14 | 0.18 ± 0.14 |
| TRANSLATION FOLLOW | 0.08 ± 0.04 | 0.04 ± 0.03 | 0.12 ± 0.08 |
| TRANSLATION MIRROR | 0.10 ± 0.02 | 0.05 ± 0.02 | 0.10 ± 0.06 |
| TOP | | | |
| THREE POINT | 0.07 ± 0.04 | 0.18 ± 0.11 | 0.22 ± 0.13 |
| FLEXION | 0.16 ± 0.09 | 0.09 ± 0.06 | 0.98 ± 0.63 |
| LATERAL BENDING | 0.40 ± 0.21 | 0.55 ± 0.51 | 0.46 ± 0.22 |
| ROTATION FOLLOW | 0.15 ± 0.15 | 0.23 ± 0.20 | 0.17 ± 0.24 |
| ROTATION MIRROR | 0.11 ± 0.09 | 0.12 ± 0.10 | 0.15 ± 0.09 |
| TRANSLATION FOLLOW | 0.06 ± 0.04 | 0.05 ± 0.05 | 0.18 ± 0.13 |
| TRANSLATION MIRROR | 0.14 ± 0.03 | 0.06 ± 0.06 | 0.14 ± 0.25 |

TABLE II: POSITION ERROR

| MIDDLE | x (mm) | y (mm) | z (mm) |
|---|---|---|---|
| THREE POINT | 0.52 ± 0.34 | 1.13 ± 1.22 | 0.65 ± 0.36 |
| FLEXION | 0.59 ± 0.31 | 1.28 ± 0.71 | 0.57 ± 0.38 |
| LATERAL BENDING | 1.35 ± 0.73 | 0.28 ± 0.16 | 0.85 ± 0.54 |
| ROTATION FOLLOW | 0.67 ± 0.67 | 0.83 ± 0.47 | 0.55 ± 0.27 |
| ROTATION MIRROR | 0.73 ± 0.67 | 0.88 ± 0.52 | 0.72 ± 0.35 |
| TRANSLATION FOLLOW | 0.26 ± 0.12 | 0.42 ± 0.20 | 0.32 ± 0.18 |
| TRANSLATION MIRROR | 0.23 ± 0.12 | 0.47 ± 0.26 | 0.32 ± 0.25 |
| TOP | | | |
| THREE POINT | 0.53 ± 0.39 | 0.61 ± 0.48 | 1.18 ± 0.57 |
| FLEXION | 0.54 ± 0.44 | 6.99 ± 3.77 | 1.55 ± 0.89 |
| LATERAL BENDING | 6.74 ± 3.90 | 0.84 ± 0.52 | 1.46 ± 1.23 |
| ROTATION FOLLOW | 2.02 ± 1.22 | 2.54 ± 1.29 | 0.80 ± 0.39 |
| ROTATION MIRROR | 1.29 ± 0.72 | 1.51 ± 0.82 | 1.06 ± 0.47 |
| TRANSLATION FOLLOW | 0.85 ± 0.60 | 0.93 ± 0.49 | 0.46 ± 0.26 |
| TRANSLATION MIRROR | 0.31 ± 0.26 | 0.25 ± 0.24 | 0.73 ± 0.39 |

TABLE III: ROM

| | NO BRACE (deg) | WITH BRACE (deg) | PERCENT ROM |
|---|---|---|---|
| FLEXION | 36.9 | 37.0 | 100 |
| EXTENSION | 24.9 | 19.1 | 76.4 |
| BENDING RIGHT | 43.0 | 35.6 | 82.6 |
| BENDING LEFT | 41.5 | 38.7 | 93.1 |
| ROTATION RIGHT | 38.0 | 22.2 | 58.3 |
| ROTATION LEFT | 42.8 | 34.5 | 80.8 |

FIG. 10E

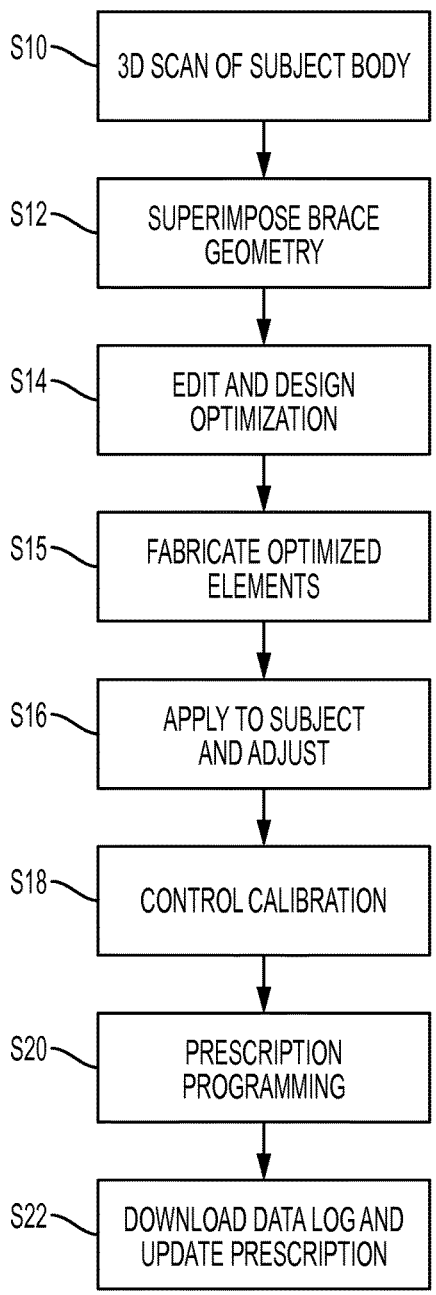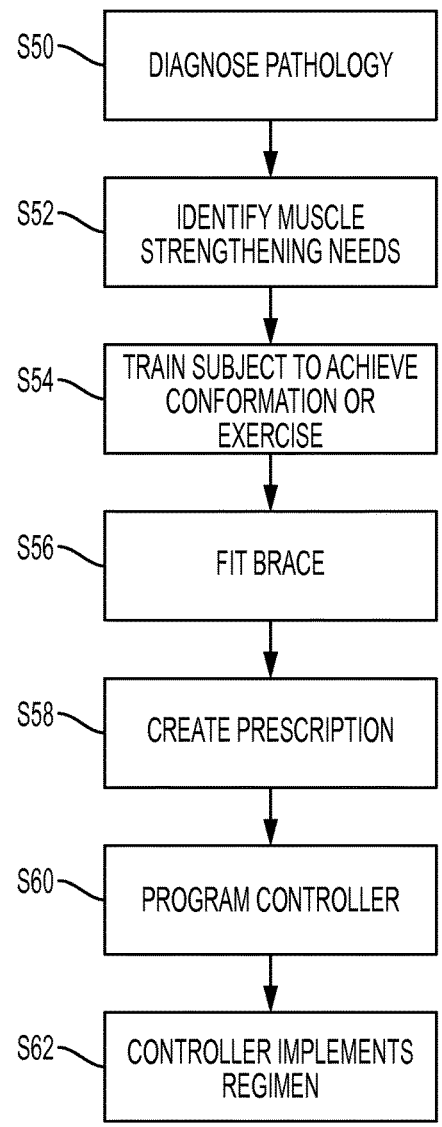
FIG. 12
FIG. 13

SPINAL TREATMENT DEVICES, METHODS, AND SYSTEMS

CROSS-REFERENCE TO RELATED APPLICATIONS

The present application is a U.S. national stage filing under 35 U.S.C. § 371 of International Application No. PCT/US2015/027634 filed Apr. 24, 2015, the content of which is hereby incorporated by reference in its entirety, which claims the benefit of U.S. Provisional Application No. 61/984,547, filed Apr. 25, 2014, and U.S. Provisional Application No. 62/067,569, filed Oct. 23, 2014, both of which are hereby incorporated by reference herein in their entireties.

FIELD

The present disclosure relates generally to rehabilitation or assistance devices, and more particularly, to systems, methods, and devices for correcting scoliosis or adjusting spinal alignment.

BACKGROUND

Passive spine braces are commonly used to treat scoliosis by helping to curtail progression of the abnormal spine curves in adolescents and prevent surgery. Conventional spine braces are generally formed of a single rigid body. Some braces apply three point loading with rotation while other braces are designed to provide traction and rotation to the spine. In general, the goals of these braces are to correct or stop the progression of abnormal curvature of the spine. However, the rigidity of these braces makes them difficult to wear for extended periods of time and interferes with typical activities of daily living. Braces have been proposed that provide flexibility, for example, SpineCor (http://www.spinecor.com) and U.S. Pat. No. 8,795,213.

In addition, core muscle strength and flexibility are important features for health and longevity. Core exercises are gaining popularity. Posture also presents health issues especially for deskbound persons and workers who perform repetitive tasks.

SUMMARY

Active wearable body brace embodiments provide selectable conformation control of the interface between the trunk of a human subject and the brace, which conformation may be varied over time and responsively to feedback and an updateable prescription. Further active wearable body brace embodiments provide selectable movement control of the interface between the trunk of a human subject and the brace with up to six degrees of freedom between elements to allow a controller to implement operations such as muscle challenges, active support, and passive-like support where actuators mimic springs. Further embodiments may also provide detection functions such as quantifying muscle weakness. The features of these embodiments may be combined in various ways to provide still further embodiments.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

FIG. 10E shows three tables that represent orientation error, position error, and range of motion (ROM).

FIG. 12 shows a set up procedure for an active brace, according to embodiments of the disclosed subject matter.

FIG. 13 shows a procedure for treating a musculoskeletal pathology, according to one or more embodiments of the disclosed subject matter.

DETAILED DESCRIPTION

Figure 1A:
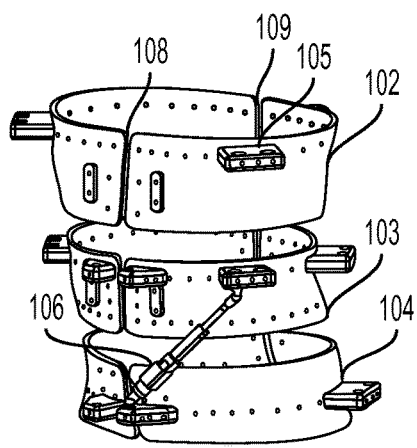
FIG. 1A shows a 3D model of a brace with actuator platforms and conforming orthotic cuff components, with a single actuator in position to show scale, according to one or more embodiments of the disclosed subject matter.

A brace presented in this application is capable of applying both forces and moments to the body at two or more locations. An active orthosis system is used in a brace. The brace can control either the force and moments applied to the body or its position and orientation. If used in position control mode, load cells may be used to evaluate the six dimensional forces/torques while achieving a certain level of correction. If used in force mode, the device can exert six dimensional corrective forces/torques on the body or zero force to the user in transparent mode.

A scoliosis brace may fit around the trunk and hips and apply counter-pressure on the abnormal curve of the spine, force movements of the trunk of the subject in various modes, limit movement, challenge the subject's muscles, and a variety of other modes under control of a programmable controller. In embodiments, a thoraco-lumbo-sacral orthosis may be provided for adolescents and worn for up to 18 hours a day.

A principle of clinical treatment with certain types of braces is that pressure on the curve from the outside will allow more normal growth of the spine. Forces may be applied by stiff members, by flexible bands or other urging mechanisms. Spine correction requires modulation of forces and moments along the curve and the need may change over time. By means of an active brace, the change may be provided. Other features may also be enabled by various brace platform embodiments such as post-surgical therapy, diagnosis, posture correction, core strengthening and others. Using programmable control, an active brace can detect requirements and respond to conditions, including following location-based or activity-based protocols. Active braces have the potential to be more comfortable by changing their configurations to allow pressure relief and movement. Cartilage health may be improved by movement.

A wearable brace of embodiments of the present disclosure can dynamically modulate corrective forces and moments along the natural curve of the spine and also respond to the effects of the brace on the spine as it adjusts over time. In embodiments, a brace includes a series of rings that are snugly attached to the human body and conform to different cross sections in the upper torso. Forces and moments may be applied to each ring using actuators mounted on adjacent rings. The rings may be "parallel-actuated" using robotic actuators, for example, "cable-driven", cable and spring-driven, "Stewart-platform", and various "compliant" mechanisms which may be combined as features in a variety of ways. In addition to applying forces, control of actuators may permit a brace to effect various static positions, permit motion in certain modes such as bending to one side and resist motion in other modes such as bending backward. Actuators can also act as springs, generating resistance to allow the subject to push against the force of a virtual spring to exercise muscles according to a program. Vibrotactile sensors may permit the subject to receive messages or prompts from a brace such as predefined vibration signal indicating the initiation of an exercise or to provide guidance to the user or rate other information. Pressure and temperature data measured from a brace as well as joint angle data may be used for closed-loop control of actuators. Pressure, temperature, and motion data may be collected wirelessly over time for patient monitoring, data mining, and planning the course of clinical treatment. Monitoring controller and data logger that interface with the brace may be wearable or may run as software on a mobile computer such as a smartphone.

Braces according to the disclosed subject matter may be used for treating adolescent idiopathic scoliosis, adult functional scoliosis, childhood scoliosis and other disorders. Embodiments may be used for core muscle strengthening exercises, posture improvement, as exoskeletons to reduce fatigue or risk of injury. Different from the conventional scoliosis braces, whose corrective forces are applied to the scoliotic curves in static manner, braces according to the disclosed subject matter braces offer dynamic sensing and modulation of the corrective forces and moments along the natural curve of the spine.

In embodiments, "parallel-actuated" rings conform to the cross sections in the upper torso and are snugly attached to the body. Corrective forces and moments are applied to each ring using actuators mounted on adjacent rings. The rings may be "parallel-actuated" using either linear actuators or cable-driven mechanisms. Underarm braces of various architectures may be configured to treat single or double curve scoliosis. For single curve scoliosis, a brace according to the disclosed subject matter may have 3 rings and for a double curve it may have 4. This concept may be extended with more rings to address more complex 3-dimensional spine curves. Instead of using separate rings, pads or bands may be used or added to a multiple-ring embodiment to apply forces (resistance, movement, etc.) to specific areas of the trunk of the subject.

In embodiments, a bottom ring sits on the waist and a top ring is positioned around the chest below the armpit. The rings may be rigidly connected through an external column or supported by the actuators or both. The brace according to the disclosed subject matter may provide multiple degrees of freedom. A tested embodiment provided six degrees-of-freedom (DOFs) and included three rings, an intermediate ring carrying six actuators to apply forces to a lower ring and six actuators to apply forces to an upper ring. Each set of six actuators defined a Stewart platform. In the tested embodiment, linear actuators were employed. Note actuators may be linear actuators driven by screws, equivalent cable-spring compounds that function as linear actuators, or other types of active actuators. Pressure and temperature data were measured by embedded sensors between the rings and the human body. Orientation and force sensors were used for monitoring and control. These sensors and actuators may be used to provide closed-loop control of the corrective forces on the spine. The pressure, motion, and temperature data were collected wirelessly over time for patient monitoring, brace compliance, data mining, and clinical treatment.

Spine correction may employ a controller that modulates forces and moments along the curve, for which the needs change over time. Thus, a programmed controller can changes the forces and moments over time according to a predefined prescription and/or in response to feedback such as indicated by detected measurements of flexibility and/or strength. Using pressure and/or force sensors (on the actuators) the subject's responses may be measured and flexibility, strength, and other parameters indicative of the subject's condition may be acquired and logged and/or used for diagnosis, and/or used by the controller for conditional control of the brace platform. Embodiments can build upon existing brace designs and technology by employing passive elastic belts and fixed elements that are custom-molded to fit the subject. These may be used in addition to active elements.

The ability to control the corrective forces along with adjustable elements such as rings also allows the device to adapt to changes in the body shape/size over time. This makes the treatment of children more effective by potentially avoiding visits to an orthotist and ensuring a fully functional fit of the brace at all times. Current braces are strictly patient-specific and cannot be re-used for other scoliosis patients. A brace according to the disclosed subject matter may be reconfigured using actuators offering versatility for various types of scoliosis or other uses as mentioned.

Note the term "brace" as used broadly herein, is intended to cover devices that engage the trunk to provide the various functions of the embodiments described herein and others, not merely the function to apply a fixed force or limit of movement as a traditional brace.

One principle of brace treatment is that pressure on the curve from the outside will allow more normal growth of the spine. Rigid braces may apply localized forces causing rib cage deformity as well as pain and skin breakdown. Embodiments of braces according to the disclosed subject matter may provide active modulation of forces/moments which can, with appropriate control strategy, mitigate the extensive localized forces applied on the body while maintaining the functionality of applying corrective forces to the abnormal curves. In addition, fixed braces typically restrict normal activities of daily living (ADLs) and are uncomfortable, hence children avoid wearing these. Braces according to the disclosed subject matter do not fully restrict the upper body motion and may be made to accommodate/follow the motion of the subject by proper control of the actuators. Current braces may not provide real-time sensor data. There are only few published works with sensors in scoliosis braces but they only provide localized information on body temperature and pressure. Braces according to the disclosed subject matter may utilize multiple sensors of different kinds (pressure, orientation, force, temperature) that can provide the pressure mapping between the device and the body, trunk motion, and temperature data all collected wirelessly over time for patient monitoring, brace compliance, data mining, and planning of the clinical treatment.

Rigid braces for scoliosis treatment may utilize corrective forces/moments generated from the preconfigured shape of the brace to bring the spine curve back to its normal position. Braces according to the disclosed subject matter also provide corrective forces/moments on the scoliotic curves but these are active instead of passive. Corrective forces/moments may be varied over time or according to predefined conditions detected by the controller. Time-varying controllable parameters can enhance the clinical and practical aspects of braces according to the disclosed subject matter.

Another feature is the motion capability. Passive braces may come with fixed shapes that fully restrict the motion of the torso. Braces according to the disclosed subject matter may have relative degrees-of-freedoms (DOFs) between rings that allow a wearer to attain a range of body motion. Braces according to the disclosed subject matter may have several types of sensors and wireless communication system that may be used for closed-loop control on actuators of the brace as well as real-time monitoring on the human-machine interface.

Advantages which braces according to the disclosed subject matter can provide include, but are not limited to: (i) effective control of corrective forces on the spine both spatially and temporally, (ii) increase wearability by allowing the upper body to be constrained in some directions but free to move in other directions, (iii) provide a way for clinical staff to monitor the spine in close-loop through sensors, (iv) eliminate the cost and need for remaking rigid braces every few months for the patients. Braces according to the disclosed subject matter may be used to treat scoliosis, kyphosis or lordosis. They may also be used during the recovery of post-spine surgery patients.

FIG. 1A shows a 3D model of a brace with actuator platforms and conforming orthotic cuff components, with a single actuator in position to show scale, according to one or more embodiments of the disclosed subject matter. Three ring elements 102, 103, and 104 are formed by respective halves divided as indicated at 108 and 109. The portions of ring elements 102, 103, and 104 permit them to be somewhat strong and rigid and still be fittable to a subject 110. Closures such as clamps or any suitable hardware may be provided to form the ring shape around the subject 110 once fitted. In embodiments, the closures (not shown) may be adjustable to permit size changes of the subject to be more easily accommodated. Note also that according to embodiments, the closures can include one or more active actuators to allow the circumference of a respective ring to be changed under control of a controller. Linear actuators (one indicated at 106) include force sensors and displacement encoders. Only one is shown but extensions 105 are provided at various points to permit the formation of two Stewart platform actuators that can move the rings 102, 103, and 104 relative to each other. As known, the Stewart platform can apply forces tending to pivot about any axis and provide forces tending to displace along any axis for a total of six degrees of freedom.

Figure 1B:
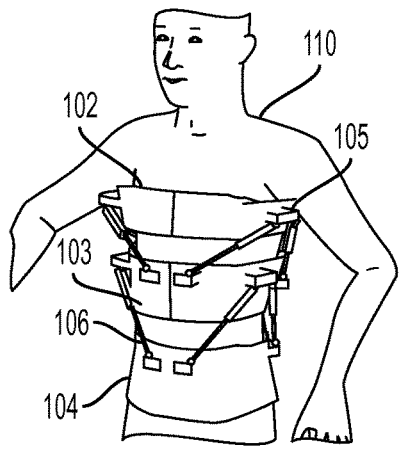
FIGS. 1B and 1C show a more figurative embodiment of the brace of FIG. 1A, in FIG. 1B fitted to a subject and in FIG. 1C, standing by itself, each showing linear actuators in place on the brace, according to one or more embodiments of the disclosed subject matter.
Figure 1C:
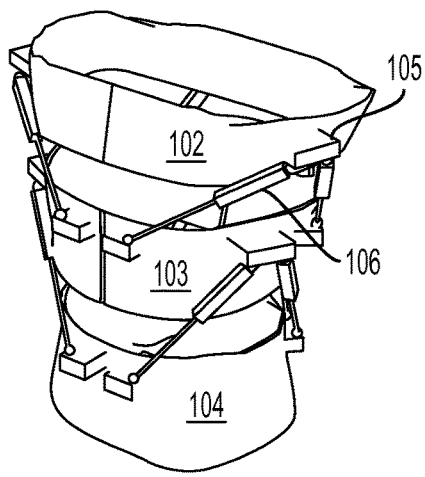
Figure 1D:
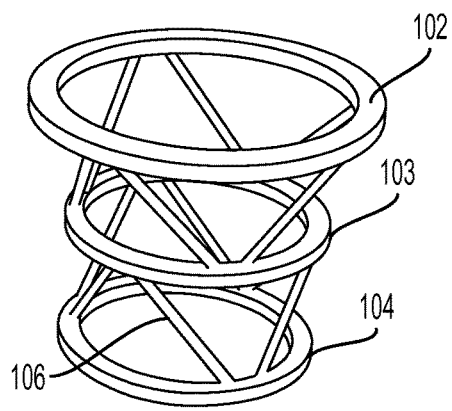
FIG. 1D shows an abstracted version of the three-ring braces of FIG. 1A and which shows two Stewart platforms that may be used, according to one or more embodiments of the disclosed subject matter.
Figure 1E:
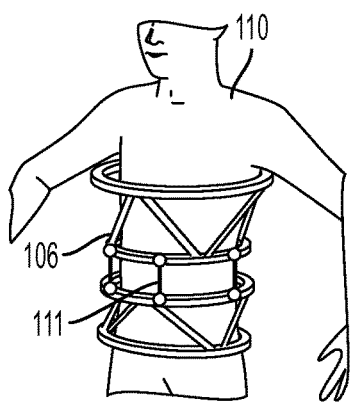
FIG. 1E shows a shows a possible design with 4 rings for correction of S-type scoliosis curves where upper and lower inner rings are rigidly interconnected and the two upper and lower outer rings are floating and articulated using the actuators or alternatively where upper and lower outer rings are rigidly interconnected and the two inner upper and lower rings are floating and articulated using the actuators, according to one or more embodiments of the disclosed subject matter.

FIGS. 1B and 1C show a more figurative embodiment of the brace of FIG. 1A, in FIG. 1B fitted to a subject 110 and in FIG. 1C, standing by itself, each showing linear actuators in place on the brace, according to one or more embodiments of the disclosed subject matter. FIG. 1D shows an abstracted version of the three-ring braces of FIG. 1A which shows the two Stewart platforms which may be used, according to one or more embodiments of the disclosed subject matter. FIG. 1E shows a shows a possible design with 4 rings for correction of S-type scoliosis curves where upper and lower inner rings are rigidly interconnected (as indicated by rigid link symbols 111) and the two outer upper and lower rings are floating and articulated using the actuators or alternatively where upper and lower outer rings are rigidly interconnected (not shown) and the two inner upper and lower rings are floating and articulated using the actuators. Although not shown, a rigid or somewhat compliant interconnection may be provided, for example, on the back side to interconnect and support the ring elements for convenient handling and also for support for certain modes of use such as resistance of certain movements. In any of the embodiments, the actuators are capable of pulling and pushing selectively under control of a controller. Any of the embodiments may include a battery pack, final controller, transceiver and any other elements required to implement the functional aspects described hereinabove and hereinbelow. In embodiments, or particular applications thereof, it may not be desired to control all six degrees-of-freedom of position afforded by a Stewart platform, for example, if some limited translation or rotation were sufficient. Then, the configuration may require fewer actuators. This may result in a trade-off between control of appropriate number of degrees-of-freedom at a cross section of the spine and the required number of actuators, i.e., thereby to simplify cost and complexity of the embodiment.

Figure 1F:
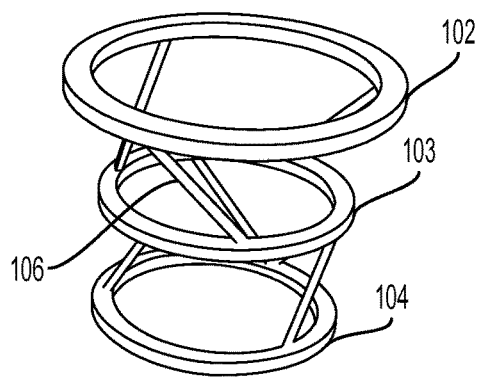
FIG. 1F shows a 3-ring configuration of a brace, where 3 actuators of a Stewart platform control the relative position of the lower and middle rings and a further 3 actuators of a Stewart platform control the relative position of the upper and middle rings, according to one or more embodiments of the disclosed subject matter.
Figure 1G:
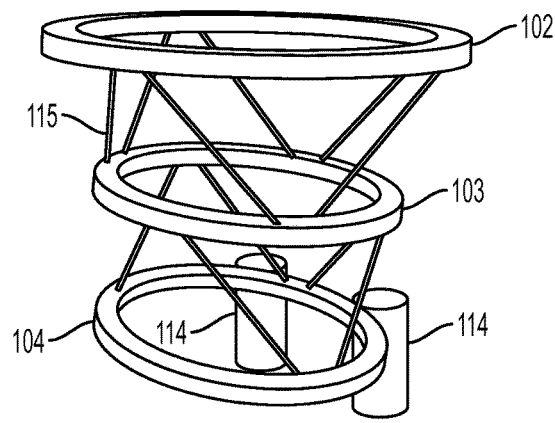
FIG. 1G shows features of cable-actuated active brace embodiments, according to the disclosed subject matter.

FIG. 1G shows a cable-driven 3-ring brace according to the disclosed subject matter for correction of C-type scoliosis. A 4-ring brace or equivalents of any of the foregoing and others may be based on the same features. Winches 114 are attached to a ring 104 and used to draw cables 115 which are routed through the rings (details not shown) to provide rotational and displacement forces. Note that springs may be positioned to oppose the force of the cables 115. For example, helical springs could surround each cable and in this way provide the ability to create both push and pull forces selectively under control of a controller. The placement of rings on the upper torso for the cable-driven braces may be similar as for Stewart-platform type braces. The fundamental difference between a cable-driven and Stewart-platform type brace is that a component leg is now replaced by a cable which may be reeled in or out by the motors. In cable-driven designs, cables transmit forces from the winches to the rings. Important benefits of cables include relatively light weight and simplicity of assembly, as opposed to assembly of legs in Stewart-platforms, which can be complex or involved. It must be noted that displacement kinematics of a cable-driven and a Stewart-platform type mechanism with similar architectures is identical. Although not shown, the configuration of FIG. 1G may have battery packs, controller, transceiver, etc.

In a cable-driven design, each cable can only pull but not push. If the goal is to control the position/orientation (force/moment) of the middle ring in a 3-ring design, a minimum of 7 (6+1) actuators is needed. This result follows from the property of systems for which the actuators can only apply unilateral forces. Using a similar argument, the 4-ring design will require a minimum of 14 (7×2) actuators. More involved cable routings where cables go from the bottom to top rings via the middle rings may be provided.

In tests of a laboratory test-bed a 3-ring cable-driven brace modeled to address a target like a C-type brace, the middle ring floated, suspended by four passive cables from a top ring. The middle ring was controlled by four motors placed symmetrically on the stationary bottom ring. A cable spool was connected to each motor shaft with cable wrapped on it to form a winch actuator. One end of each cable was connected to a winch spool while the other end was connected to the middle ring. The middle ring in this experiment was targeted to be controlled in three degrees-of-freedom of planar translation with respect to the two fixed rings. The system was placed in a motion capture system with markers attached to the moving ring. The motion of the floating ring was observed and quantified while the positions of four motors were controlled to deliver a sinusoid motion pattern. This test evaluated a simple cable-actuation architecture that provided a limited number of degrees-of-freedom. The results showed that the ring was capable of translation in the transverse plane. The test bed was constructed out of 1/16 in.×1 in. aluminum stays. As a result of this thin unsupported cross-section, the ring exhibited some additional motion normal to the desired path due to buckling of the members under tension. This may be prevented by providing an additional constraint to the members, such as a strap that would hold the rings to the body, a small crease in the cross section to improve stiffness, or by laminating the stays in plastic as this would additionally add to comfort of the brace. The test-bed may be extended to include a larger number of actuators as well as different configurations of the cable routings to investigate the issues of practical implementations in the desired motions/forces in the intermediate rings.

Figure 2:
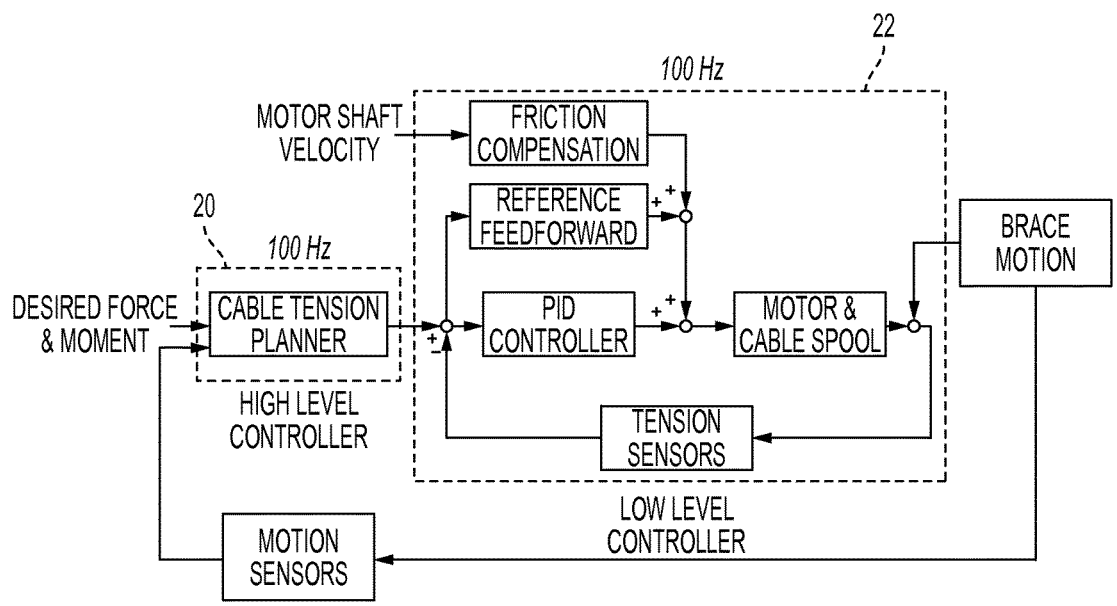
FIG. 2 shows a control architecture for controlling embodiments of the disclosed subject matter.

FIG. 2 shows a control architecture for controlling embodiments of the disclosed subject matter. The two-level control architecture has a 'high-level tension planner' 20 and a low-level tension controller' 22 using in-line tension sensors in the cables. This control architecture is suitable for implementation for real-time control.

Figure 3B:
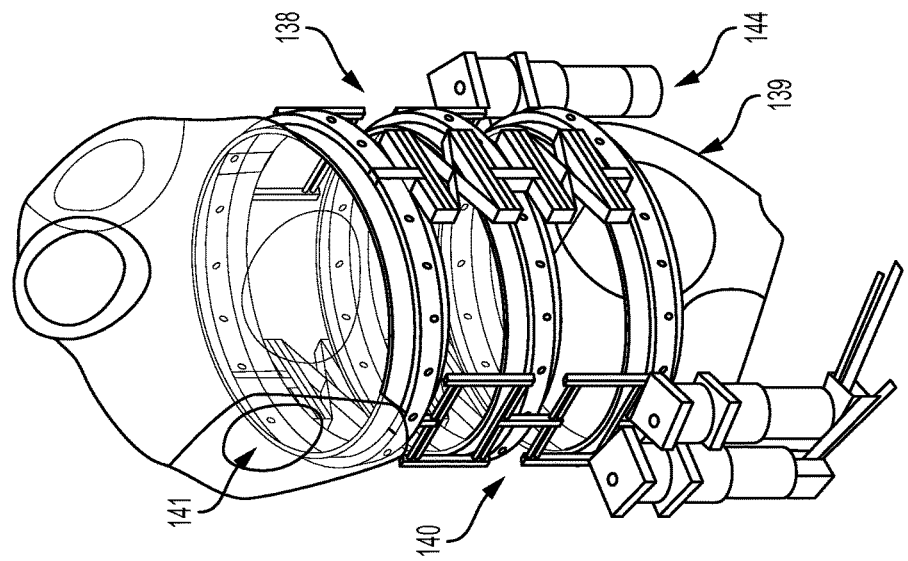
FIGS. 3A and 3B show 3-ring braces with compliant components, according to embodiments of the disclosed subject matter.
Figure 3A:
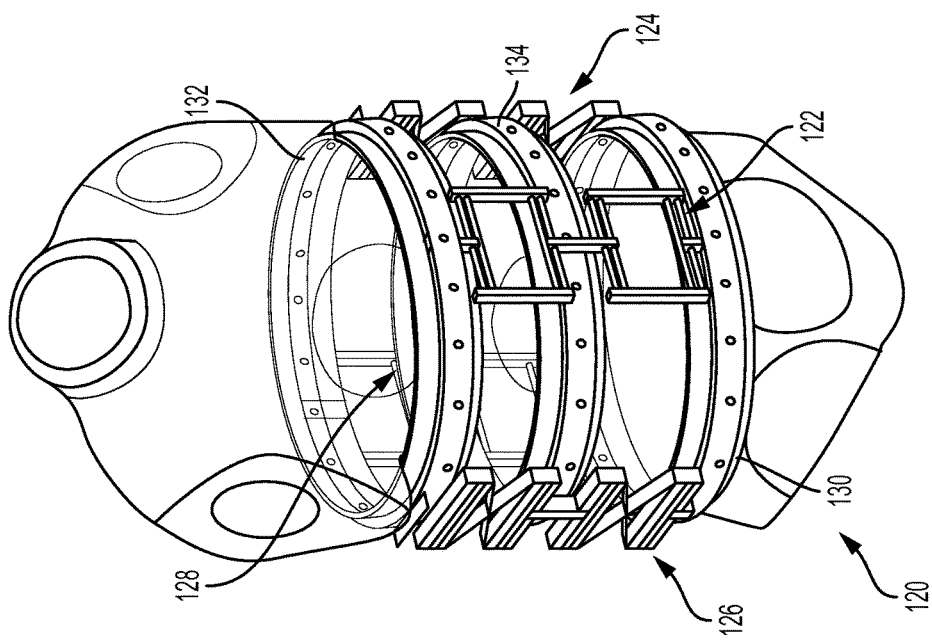

FIG. 3A shows a 3-ring compliant brace 120 consisting of four stacks of compliant components 122, 124, 126, 128 between the bottom 130, middle 134, and top 132 rings. The square shaped stacks 122, 128 allow the rings to translate up and down but result in high stiffness in other directions of translation and rotation. The diamond-shaped stacks 124, 126 allow up and down translation and forward bending but result in high stiffness in other directions. When the four stacks 122, 124, 126, 128 are connected in parallel between the three rings 130, 132, 134, due to the high stiffness of the brace in lateral directions, the C or S curve of the spine becomes naturally constrained to be closer to a straight configuration while the brace allows flexion and extension of the human body (bending forward or backwards). From this example, we can see that compliant mechanisms may be designed to create constraints in certain directions while allowing motion in other directions using fewer and lightweight components compared to rigid mechanisms. FIG. 3B shows a variant in which the types stacks of compliant components 138, 139, 140, 141 are switched between sides and front-back. FIG. 3B also shows an example of emplacement of winches 144 for cable actuated embodiments. The compliant brace in FIG. 3A can provide forces and moments to provide correction in the coronal plane. Unlike traditional braces, however, the compliant brace also allows some freedom in overall motion in the sagittal plane to allow more ADL. Furthermore, the passive spring-back stiffness of the compliant mechanism may be tuned to provide some restorative force to the spine. FIG. 3B embodiment provides constraint and spring-back stiffness, but actuators can apply forces on the rings to selectively alter its stiffness in desired directions. The forces are primarily in motion directions but can also be in constraint directions, above and beyond what is attained passively. Sensing may be integrated within the system using strain gauges in individual compliant elements to track the posture of the user. In contrast to the cable-driven and Stewart-platform brace according to embodiments of the disclosed subject matter, the hybrid brace according to the disclosed subject matter relies on both actuation and passive stiffness of the compliant elements to provide corrective forces and moments to the spine through the floating rings. Compared to fully actuated brace concepts, the advantage of combining these elements is reduced complexity, weight, and required power.

In any of the embodiments, thin (0.2 mm) flexible resistive pressure sensors may be placed between the brace and the human body, distributed around each ring. These sensors may determine areas where the brace is in contact with the body and the resultant force. Shear sensors may also be used and emplaced within the interior of each ring. The sensors may be positioned at particular rings and/or at locations desired based on the particular treatment or other function to be performed by the active brace.

In one or more embodiments of the disclosed subject matter, an active thoracolumbosacral orthosis (i.e., a dynamic brace) is used to treat and correct, among other things, abnormal postures and the human spine, as often seen in adolescent idiopathic or neuromuscular scoliosis. In addition, the dynamic brace can open up new treatment methods for the human spine which are currently not used due to the features of static designs. In one or more embodiments, the dynamic brace can utilize two Stewart-Gough platforms in series, each of which may be controlled independently, either in position or force modes. The dynamic brace can provide forces/torques on different regions of the spine to modify the posture. Additionally or alternatively, it can control the motion of different regions of the spine through independent control of the degrees-of-freedom of each platform using, for example, six parallel actuators.

The dynamic brace disclosed herein is capable of applying both forces and moments to the body at two locations. The dynamic brace can control the force and/or the moments applied to the body, or it can control the body's position and orientation. If used in position control mode, load cells included in the dynamic brace may be used to evaluate the forces and/or torques (e.g., six dimensional forces/torques) while achieving a certain level of correction. If used in force mode, the device can exert forces and/or torques (e.g., six dimensional corrective forces/torques) on the body or a zero force to the user in transparent mode.

The dynamic brace can provide controlled motion or force at selected segments of the human spine. For example, the brace may be made in three segments, using semi-rigid ¼ inch fused deposition modeling (FDM) acrylonitrile butadiene styrene (ABS), separated by a 4 cm gap in the neutral position. Of course, other materials and fabrication techniques for forming the brace segments are also possible according to one or more contemplated embodiments. For example, the brace segments may be sheet formed polyethylene.

A subject's torso may be scanned to create a 3D model, which can then be used to manufacture the segments of the brace. Each segment can have support a series of holes along the circumference at, for example, 10° increments. This can allow for increased flexibility in the placement of the actuator mounts, which can attach to some of the holes. Optionally, the dynamic brace may be lined with plastazote polyethylene foam for comfort.

The mounts for the linear actuators can also be made from FDM ABS. For example, the linear actuators may be capable of providing a peak force of 55 N and a peak speed of 5 mm/s with a 5 cm stroke length (e.g., L12-50-210-12-P actuator from Firgelli). At the base of each actuator, a load cell (e.g., LCM200 load cell from Futek) and a conditioning board (e.g., ICA6H board from Mantracourt) may be mounted. Each actuator can have a universal joint at the base and a spherical joint at the top. The actuator's position feedback and load cell voltage may be multiplexed and sent to a control board (e.g., sbRio-9626 board from National Instruments). For example, the motors may be driven at 12 V using a 1000 Hz PWM signal through a small driver (e.g., TB6612FNG driver from Toshiba).

In addition to the load cells specifically mentioned above, the dynamic brace can include additional sensors to provide increased data for control and/or therapeutic/diagnostic purposes. For example, force sensing resistors may be placed around the inner surface of the brace to measure the interaction forces between the device and the body during operation. Together with the load sensors placed at each actuator, force mapping between the actuator force and the force exerted on human body may be achievable qualitatively. It can also help prevent excessive local pressure applied to the body from the device by real time monitoring. Alternatively or additionally, position and/or orientation sensors may be added to the brace to reduce the computational load in computing the forward kinematics and can potentially be used to capture user intention for active motion adaptation of the device.

Figure 5:
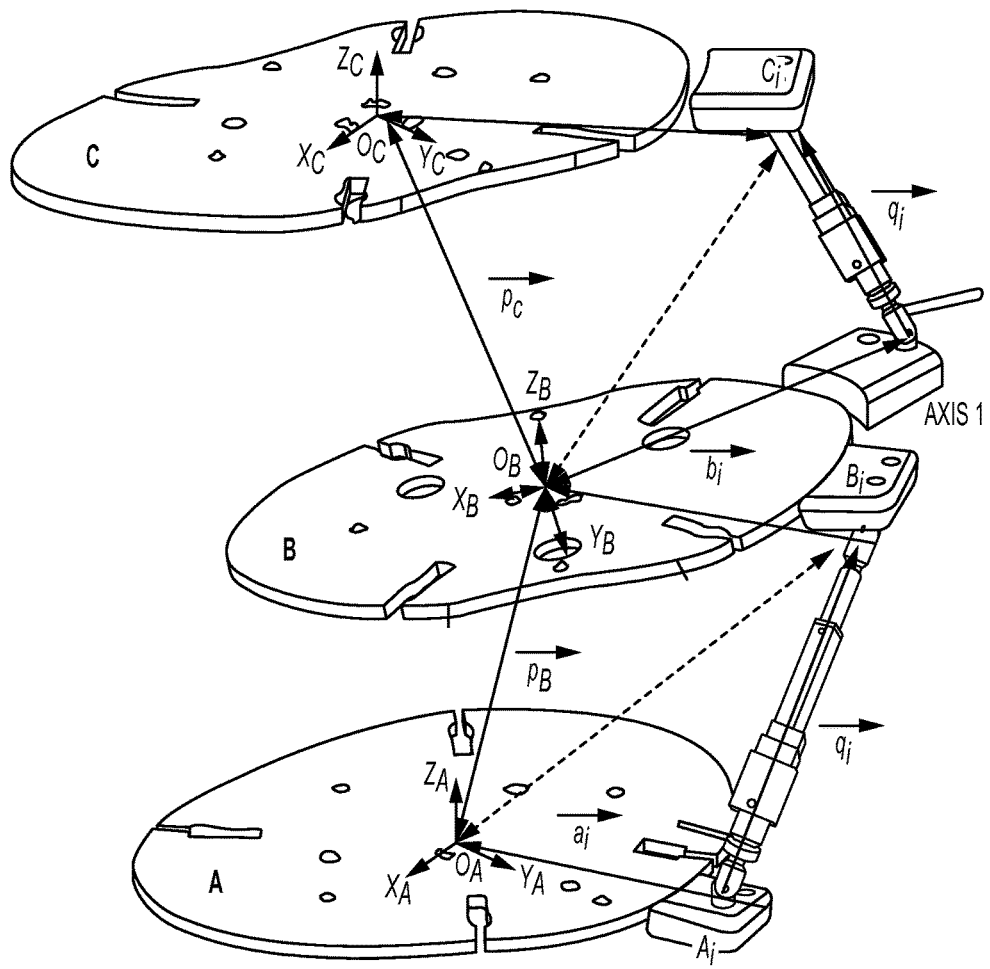
FIG. 5 shows the geometry and parameterization of a Stewart platform which may be used in a dynamic brace, according to one or more embodiments of the disclosed subject matter.

In one or more embodiments, the dynamic brace system can include two parallel platforms connected in series. Such a configuration has a total of twelve active degrees-of-freedom, which may be controlled by, for example, twelve linear actuators. The architecture of each parallel platform follows the kinematic structure of a 6-6 Stewart-Gough platform where all the limbs share identical kinematic chains of UPS, as illustrated in FIG. 5. The parameterization and dynamics presented below apply to the lower parallel platform, but such parameterization and dynamics may be extended to the top platform in a similar manner. Each limb connecting the fixed base A to the moving platform B forms a kinematic loop which may be expressed in the vector form as:

$$q_i = p_B - a_i + R_B b_i, \quad i=1, \ldots, 6 \qquad (1)$$

with $P_B = [P_B x, P_B y, P_B z]^T$ being a position vector, $R_B$ being a rotation matrix formed by three rotation angles ($\psi_B$, $\theta_B$, $\phi_B$), $q_i$ being a vector with magnitude $q_i$ along a unit vector along the leg, $q=[q_1, q_2, q_6]^T$ being the vector of actuated joint coordinates and $X_B = [P_B x, P_B y, P_B z, \psi_B, \theta_B, \phi_B]^T$ being the vector of moving platform motion variables. The rotation of the moving platform is defined by pitch-roll-yaw angles about the axes of base platform coordinate frame. For inverse kinematic analysis, the moving platform position $P_B$ and orientation $R_B$ are given and the problem is to solve for the joint variables, $L=[l_1, l_2, l_3, l_4, l_5, l_6]^T$. The length of each limb $l_i$ may be expressed as a norm of vector $q_i$:

$$l_i^2 = q_i^T q_i = [p_B - a_i + R_B b_i]^T [p_B - a_i + R_B b_i] \qquad (2)$$

Hence, each limb length may be uniquely determined for given position and orientation of the moving platform. For forward kinematic analysis, the joint variables $l_i$ are given and the problem is to solve for $X_B$ of the moving platform. For example, an iterative numerical solver may be used with screw axis representation of the rotation matrix. $X_B$ is redefined with screw coordinates as:

$$X_B = [P_B x, P_B y, P_B z, s_x, s_y, s_z, \theta]^T \quad (3)$$

in which $s_x$, $s_y$, $s_z$, and $\theta$ are obtained from the rotation matrix:

$$\theta = \cos^{-1} \frac{r_{11} + r_{22} + r_{33} - 1}{2} \quad (4)$$

$$s_x = \frac{r_{32} - r_{23}}{2\sin\theta},$$

$$s_y = \frac{r_{13} - r_{31}}{2\sin\theta},$$

$$s_z = \frac{r_{21} - r_{12}}{2\sin\theta}$$

The seven equations to solve for forward kinematics are:

$$E_i = -l_i^2 + q_i^T q_i = 0 \quad (5)$$
$$= -l_i^2 + [p_B + R_B b_i - a_i]^T [p_B + R_B b_i - a_i] = 0$$

for
$i = 1, \ldots, 6$
$$E_7 = \hat{s} \cdot \hat{s} = s_x^2 + s_y^2 + s_z^2 = 1$$

Nonlinear least-square optimization routines may be used to minimize $\frac{1}{2}\Sigma E_i$. The multiplicity of the solution may be resolved by iteratively comparing the solution to the one obtained from a previous step. If the error is within a prescribed threshold, that solution may be chosen. The Jacobian matrices may be computed from velocity loop closures, which are directly obtained by differentiating Eqn (1) as follows $$\dot{p}_B = \dot{q}_i - \omega_B \times R_B b_i \text{ for } i=1, \ldots, 6 \quad (6)$$

in which angular velocity $\omega_B$ of $\mathbb{B}$ with respect to $\mathbb{A}$ is:

$$\omega_B = \begin{bmatrix} \omega_1 \\ \omega_2 \\ \omega_3 \end{bmatrix} = \begin{bmatrix} \dot{\psi} - s\theta \\ c\psi\dot{\theta} - s\psi c\theta\dot{\psi} \\ -s\psi + c\psi c\theta\dot{\phi} \end{bmatrix} \quad (7)$$

The Jacobian has the following structure:

$$L = J\dot{X}_B, \; J = \begin{bmatrix} \hat{q}_1^T & (b_1 \times \hat{q}_1)^T \\ \hat{q}_2^T & (b_2 \times \hat{q}_2)^T \\ \hat{q}_3^T & (b_3 \times \hat{q}_3)^T \\ \hat{q}_4^T & (b_4 \times \hat{q}_4)^T \\ \hat{q}_5^T & (b_5 \times \hat{q}_5)^T \\ \hat{q}_6^T & (b_6 \times \hat{q}_6)^T \end{bmatrix}_{(6 \times 6)} \quad (8)$$

The static wrench of the moving platform may be also obtained using Jacobian and applying principle of virtual work, assuming the limb applies a force only along the limb axis.

$$F = J^T \tau \quad (9)$$

in which $\tau = [\tau_1, \tau_2, \ldots, \tau_6]^T$ is the actuator force vector, and $F = [f_x, f_y, f_z, m_x, m_y, m_z]^T$ is the output wrench from the manipulator.

The dynamics of the system may be determined using Lagrange's method applied to the limbs and the platform. For the limb dynamic model, each limb is considered to be a cylinder and a piston with the center of mass located at a distance of $c_{i1}$ and $c_{i2}$ from the bottom and the masses are denoted by $m_{i1}$ and $m_{i2}$, respectively. The kinetic and potential energy for the limbs and the platform are first derived followed by computing the Lagrangian. Once the equations of motion for the limb segments and the platform segment are obtained, the closed form dynamic equations of motion of the whole system may be determined.

In one or more embodiments, two control modes may be implemented to articulate the dynamic brace system. For example, the brace system may be controlled via a motion control mode and/or a force control mode. Each limb can have built-in sensors to detect its joint displacement or applied force by the joint actuator and transmit the resulting data to a controller. Such data may be used by a closed-loop controller in either or both control modes. The upper and lower parallel platforms can have their own motion and force controllers, which can operate independently. The control system (e.g., control board) and other electronics associated with the dynamic brace may be sufficiently compact so as to be wearable by the user.

Figure 6:
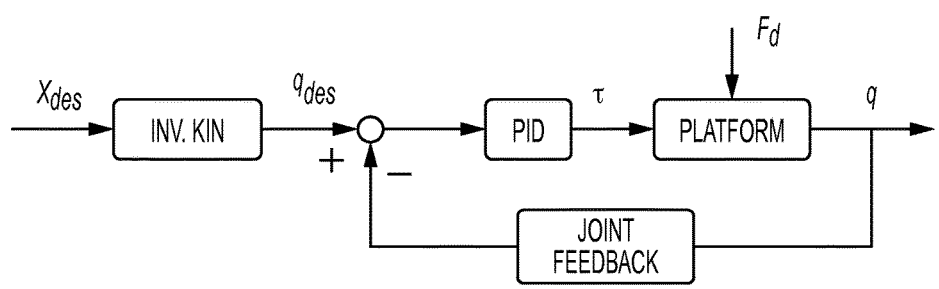
FIG. 6 is a schematic diagram of a PID controller implemented in joint space for motion control of a Stewart platform for use in a dynamic brace, according to one or more embodiments of the disclosed subject matter.

An example of a control architecture for motion control is shown in FIG. 6. Since direct measurement of motion of the platform requires additional Cartesian motion sensors, the controller may be developed in joint space using active joint position feedback. The dynamic formulation of the system is transformed into the joint space formulations owing to the Jacobian being square and invertible assuming the non-singular configurations in the operating workspace. The desired motion of the platform $X_d$ may be mapped into the joint space variable $q_d$ using inverse kinematics. The error is may be measured as the difference between the desired joint motion and the actual joint motion. These errors are a result of external disturbances or geometric mismatch in the model. A PID controller can generate the joint torques necessary to drive each actuator and the controller gains may be experimentally tuned.

Figure 8:
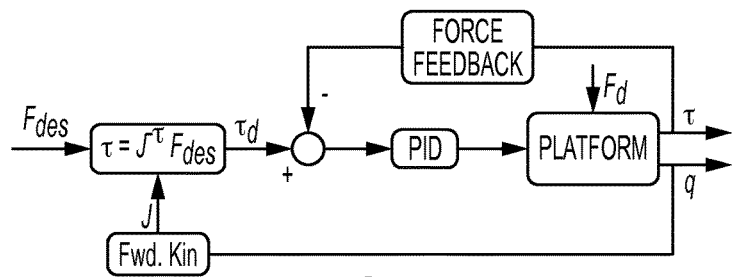
FIG. 8 is a schematic diagram of a PID controller implemented in joint space for force control of a Stewart platform for use in a dynamic brace, according to one or more embodiments of the disclosed subject matter.

An example of a control architecture for force control is shown in FIG. 8. It is designed to control the platform output force/moments in a quasi-static manner. The Jacobian may be used to compute the desired joint torques based on desired output force/moment of the platform, which was computed in real time from limb position feedback and forward kinematics. This quasi-static control approach may work well for applications where the bandwidths of both motion and force control are fairly low.

Although the dynamic braced disclosed herein may be particularly applicable to spinal correction and adjustment, one of ordinary skill in the art will appreciate that other applications enabled by the dynamic brace are also possible. For example, the brace may be used in position mode under X-ray to determine the stiffness of the spine, rib cage, and soft tissues together under six degree-of-freedom (DOF) loading to better inform how forces should be applied through dynamic braces or conventional rigid braces.

Examples

The position and force controllers were tested to determine their accuracy. In addition, a range of motion study was performed by a human subject with the force controller. The coordinate frame of the brace is oriented at the center of the bottom segment with the x-axis to the right, the y-axis towards the anterior, and the z-axis vertically upwards. The displacements and rotations reported are relative to the corresponding axes of the respective segments in the neutral position, in the bottom coordinate frame. Rotation angle $\phi$, $\theta$, $\psi$ are about z, y, and x respectively. For tests without a person wearing the device, ¼ in. plywood sheets cut to the brace's shape were placed inside the brace to improve rigidity.

Figure 7:
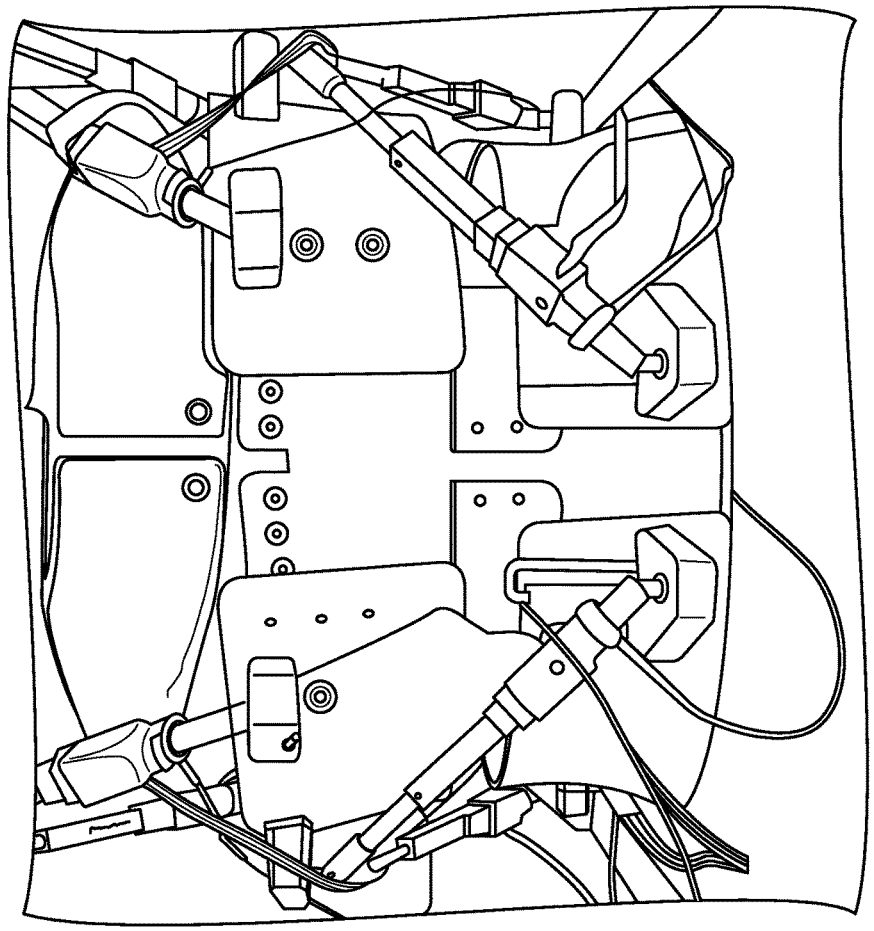
FIG. 7 shows an image of a subject wearing a 3-ring brace according to embodiments next to a force evaluation testbed with coordinate frame of the load cell.
Figure 7:
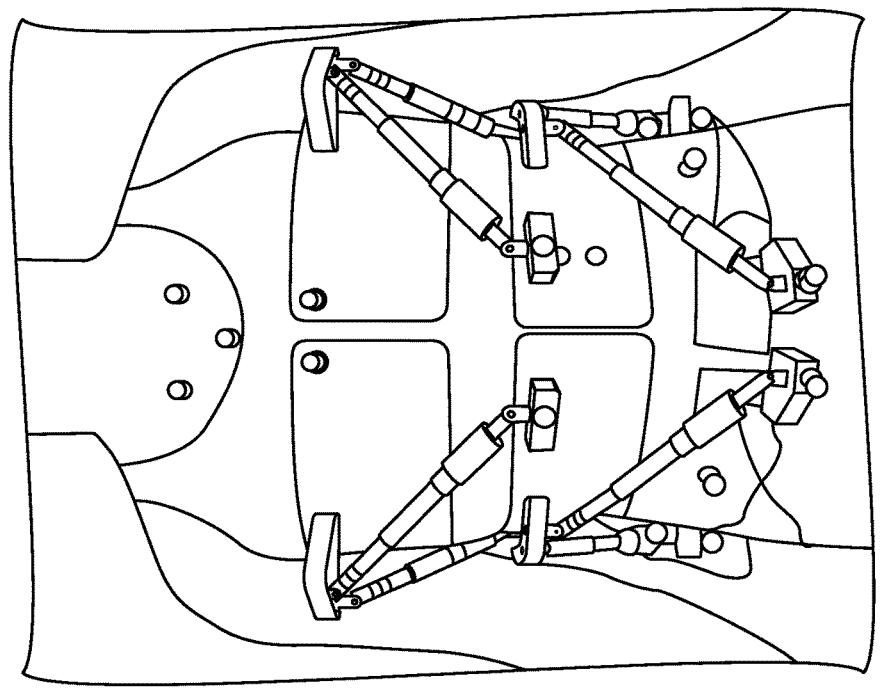

The force controller validation utilized a test bed where the middle and bottom segments were attached to each other using a 6 axis force/torque sensor (ATI, Mini45) in the brace's neutral position, as shown in FIG. 7. The brace was then driven to follow a force/torque: $-30 \leq F_x, F_y, F_z \leq 30$ N and $-1.5$ Nm$\leq M_x, M_y, M_z \leq 1.5$ nm, 2 three dimensional force/torque. The calculated force/torque from the load cells were then compared to the force/torque sensor to determine the sensor error, and the commanded force/torque profile to evaluate tracking error.

Figure 9A:
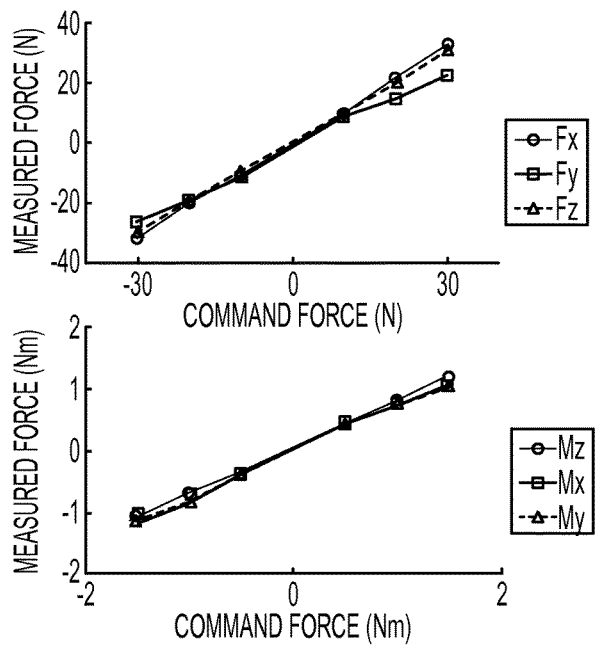
FIG. 9A shows graphs of the command force (dashed-black) and measured force (solid-blue) in a static pose from an ATI F/T sensor of a dynamic brace, according to one or more embodiments of the disclosed subject matter.
Figure 9B:
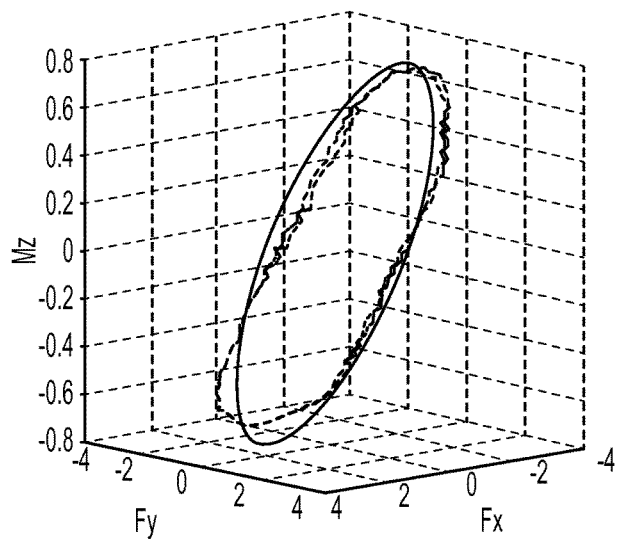
FIG. 9B shows a graph of desired and measured forces in the Fx, Fy, and Mz planes of a dynamic brace, according to one or more embodiments of the disclosed subject matter.

The force controller was able to follow the commanded force/torque (f/t) profile for one directional inputs with less than 4% average error as shown in FIG. 9A. Three dimensional f/t profile showed slightly bigger errors compared to the one directional f/t test but still within an acceptable error range ($\leq 7\%$), as shown in FIG. 9B. The compliance in the device seems to be the main source of error in three dimensional f/t testing as slight deformation from the brace was observed. Any structural deformation would likely result in changes in geometry which is difficult to capture and be reflected for real time control. The local stiffness may be increased in areas where such deformation may be likely to occur.

The position controller was tested by moving the brace through a range of translations and rotations. Planar rotation and translation in the transverse plane was tested as this mimics traditional three point loading in spine braces. Flexion and lateral bending were tested to compare bending in a brace. The last series of tests were for isolated translations and rotations. For both, the upper Stewart Platform either performed the same task (follow) or the opposite task (mirror) as the lower Stewart Platform. The motion was recorded through potentiometers on the motors as well as a motion capture system (Vicon, Bonita). The translation and rotation of the middle and top segments relative to the neutral position were recorded and analyzed in the bottom coordinate frame.

Figure 10A:
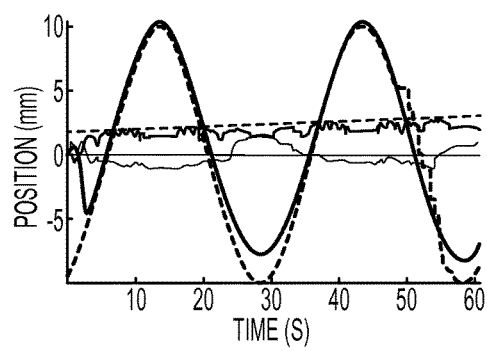
FIG. 10A is a graph of the command (dashed line) and Vicon (solid line) results from three pt. loading tests showing the XYZ position of the middle segment origin of a dynamic brace, according to one or more embodiments of the disclosed subject matter.
Figure 10B:
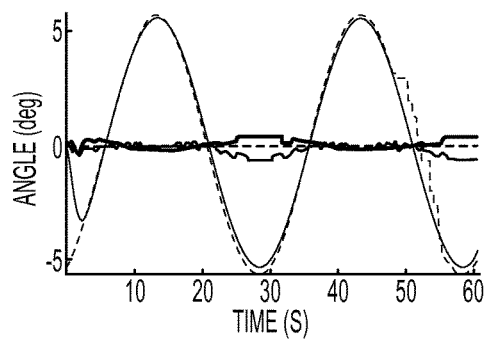
FIG. 10B is a graph of the command (dashed line) and Vicon (solid line) results from three pt. loading tests showing the rotation angles of the middle segment of a dynamic brace, according to one or more embodiments of the disclosed subject matter.
Figure 10C:
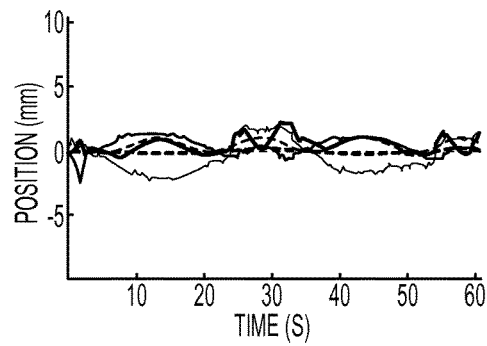
FIG. 10C is a graph of the command (dashed line) and Vicon (solid line) results from three pt. loading tests showing the position of the top segment origin of a dynamic brace, according to one or more embodiments of the disclosed subject matter.
Figure 10D:
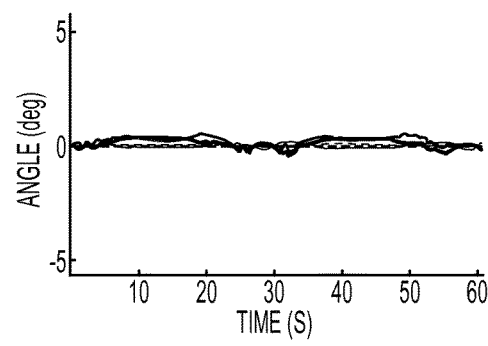
FIG. 10D is a graph of the command (dashed line) and Vicon (solid line) results from three point loading tests showing the rotation angles of the top segment of a dynamic brace, according to one or more embodiments of the disclosed subject matter.

The position controller was able to follow all paths with less than 1° of average error for all tested trajectories, as shown in FIG. 10E, Table I. For translational motions, the average positioning errors were sub-millimeter. With rotational paths, average positioning error was higher for both platforms, while still within the millimeter range, as shown in FIG. 10E, Table II. These errors were most marked in the top segment, as errors from the middle segment would also appear here. Compliance in the device may be a likely source of error. Alternatively or additionally, a mismatch between the initial configuration of the model and the actual system may also be a source of error. For flexion if the distance between the middle and the top segment was larger than modeled, then for a rotation of the middle segment the top segment would translate more in the y and z directions than expected. Similarly if the distance was smaller the translation would be lower than expected resulting in greater error. This appears for both flexion (y, z) and lateral bending (x, z). Improved calibration may reduce these errors. In addition, the top segment was capable of remaining nearly stationary while the middle segment was moved, as shown in FIGS. 10C-10D. The brace was also capable of being robust to disturbances as seen in the initial offsets and recovery in FIGS. 10A-10B.

The range-of-motion (ROM) was tested to determine the motion allowed by the brace. A healthy individual, without scoliosis, had markers applied to their anterior superior iliac spines, sacrum, sternoclavicular joints, and the inferior border of the manubrium. The subject bent to his maximum in the frontal (lateral bending), sagittal (flexion/extension), and transverse (vertical rotation) planes. The maximum change in angle between the pelvis and sternum were then compared for all three motions with and without the brace.

In most cases, the device was capable of providing more than 75% of the subject's normal ROM. However, this was not the case for rotation to the right, as illustrated in FIG. 10E, Table III. Rotation had the most reduction in ROM. This reduction could result from the rigidity of the brace in the area it covers, restricting a small subset of the vertebrae while allowing motion in the uncovered regions. Extension was also notably reduced. A possible cause may be the tendency to inhale when extending and thereby increasing the tension in the brace. However, the ROM presented here is still increased as compared to passive (e.g., rigid) braces.

In one or more embodiments of the disclosed subject matter, the use of a dynamic brace with appropriate control strategies may be effective to reduce the time the brace needs to be worn by the user (i.e., from the 12-16 hours per day required by conventional passive braces) without negatively impacting patient outcomes.

Figure 4:
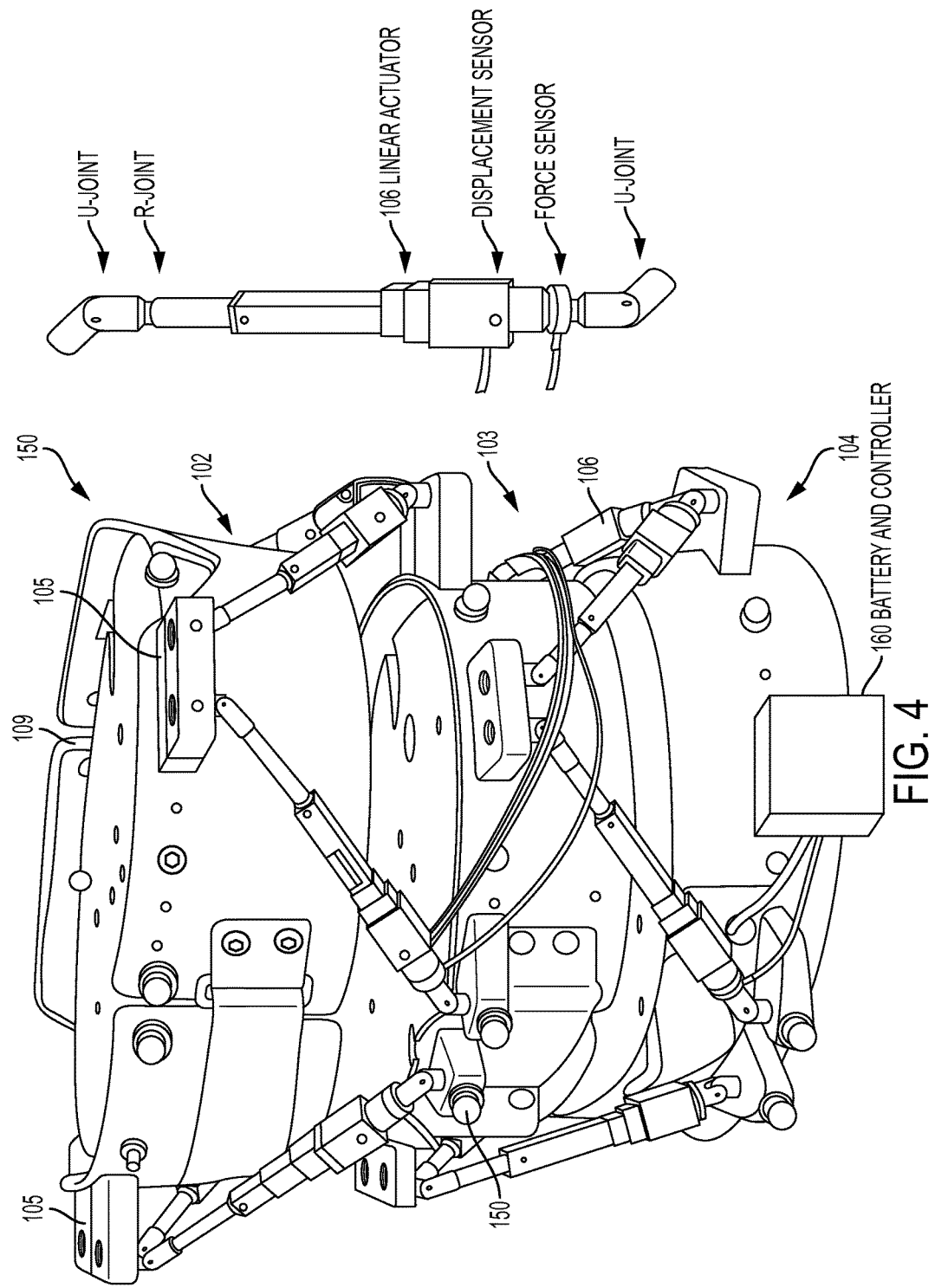
FIG. 4 shows a 3-ring brace with dual Stewart platforms based on linear actuators next to an enlarged view of a linear actuator, according to embodiments of the disclosed subject matter.
Figure 11B:
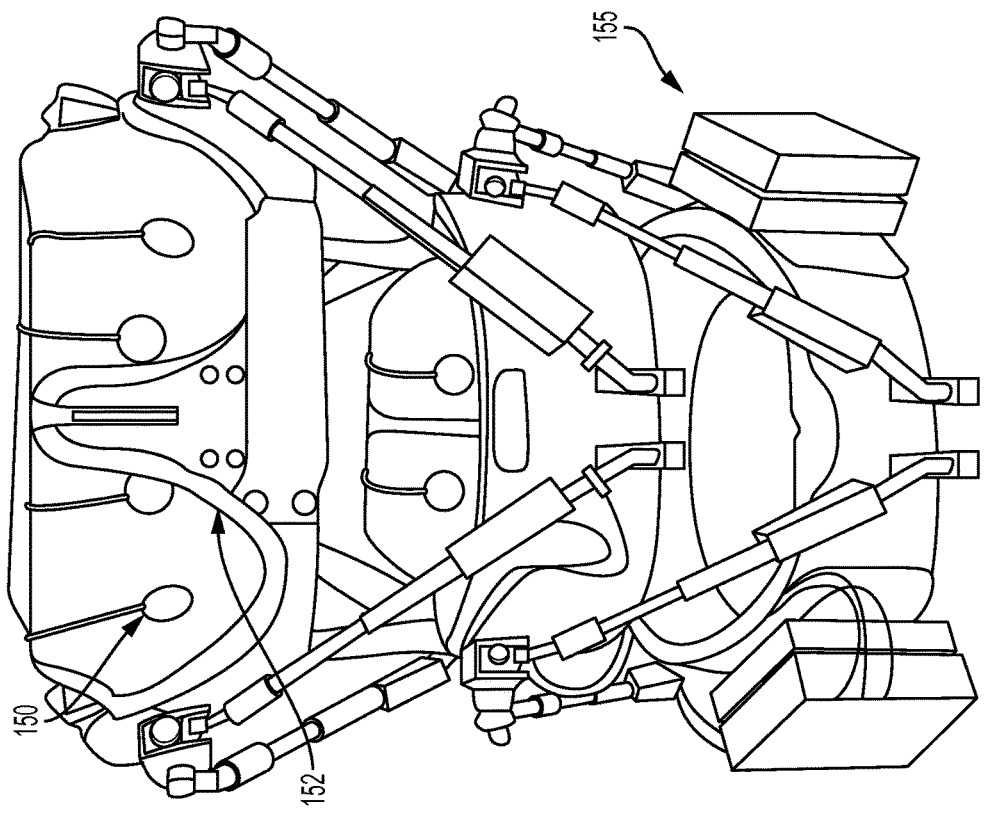
FIGS. 11A, 11B, and 11C show top and rear views, and a front view when worn by a subject, respectively, of the embodiment of FIG. 4, according to one or more embodiments of the disclosed subject matter.
Figure 11A:
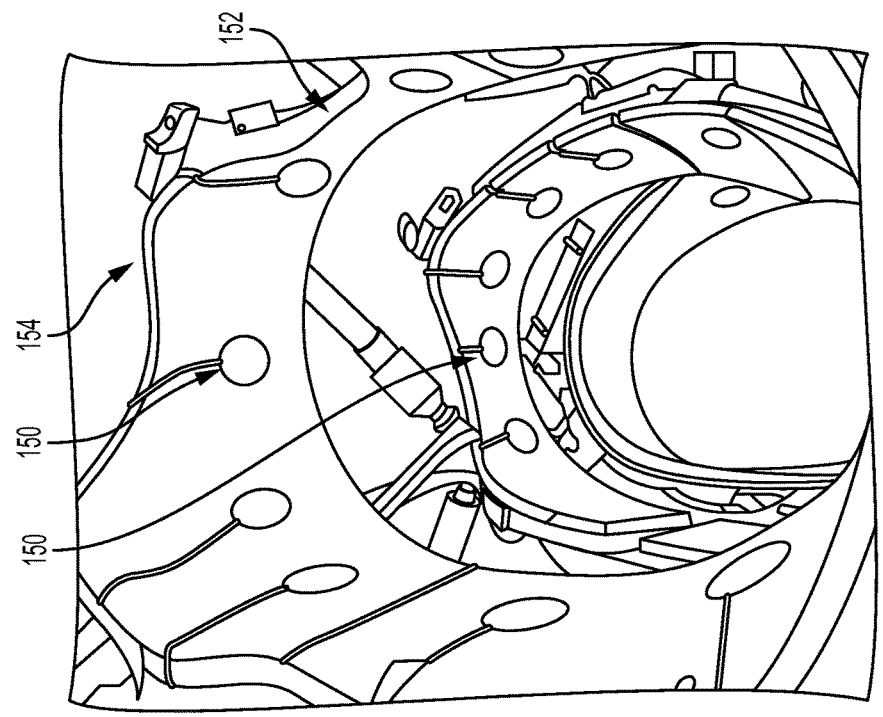
Figure 11C:
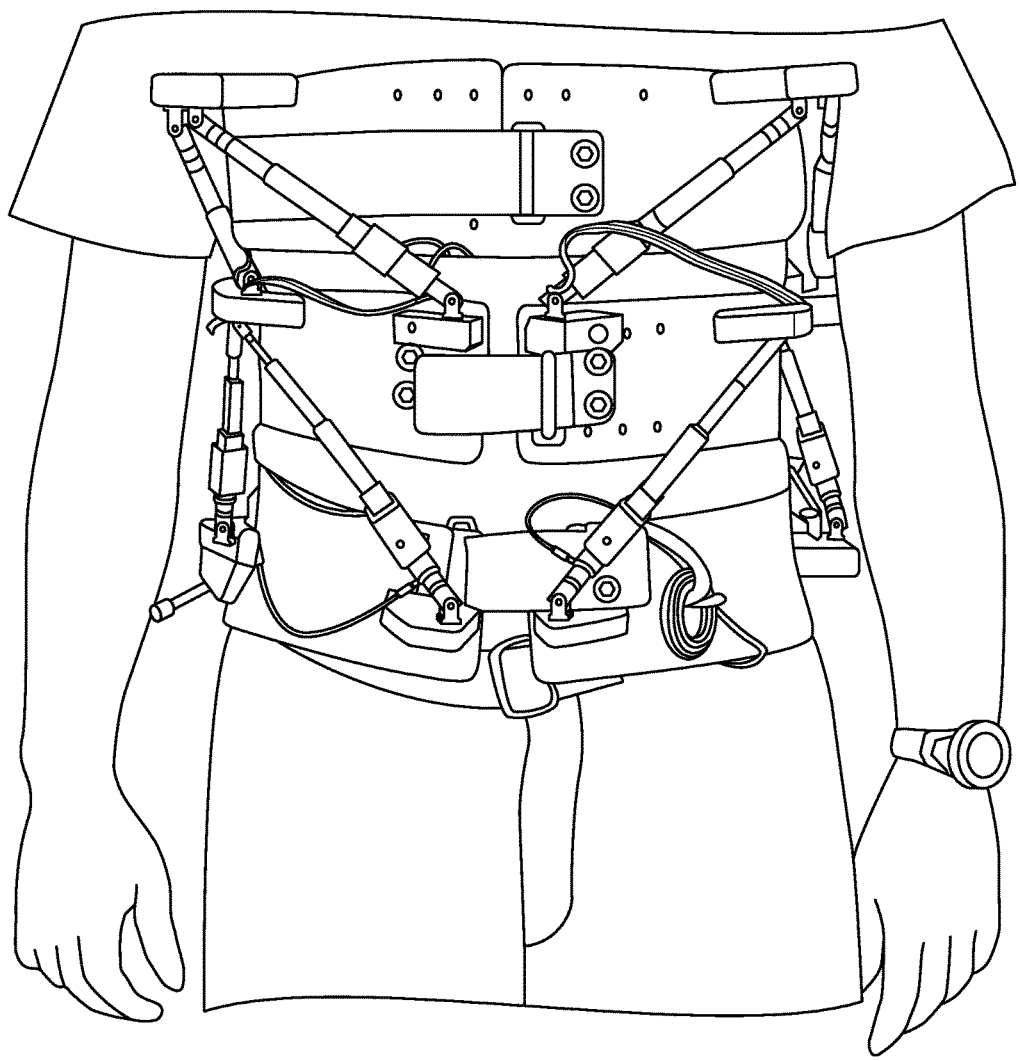

FIGS. 11A and 11B show top and rear views of the embodiment of FIG. 4, according to one or more embodiments of the disclosed subject matter. A cutouts for the shoulder blade is indicated at 152. Two are provided. Sensors on the inside are indicated at 150. Temperature and pressure sensors are distributed around the inside of the rings 154. Controller boxes, one of which is indicated at 155, are attached to a bottom ring. FIG. 11C shows a subject wearing the brace embodiment of FIGS. 11A-11B.

Additional embodiments may be provided in which actuators generate a force on other brace elements such as pads, bolsters, etc. which may be supported on extension arms and the like. Simplified embodiments may employ active or passive shaping, sizing, and positioning of the brace elements with sensing to create a feedback system that indicates to the subject whether the subject's body conformation fits a prescribed target. The pressure sensors inside the brace may indicate an amount and areas of applied force and determine whether the subject is relaxing away from a prescribed target conformation.

FIG. 12 shows an initial process for providing a subject with an active brace according to embodiments of the disclosed subject matter. At S10, the body of the subject is scanned, for example by using a laser or multi-camera capture system. A 3D model is generated in a computer at S12 and a brace is superimposed on the resulting geometry. This may be supported by software that generates a shell a certain distance from the body. The design may be edited automatically by anatomy-aware software and/or by a specialist at S14. At S15, the custom components of the brace are fabricated, for example by 3D printing or by thermally shaping polyethylene sheets and bolting on attachments, for example and the custom parts are assembled with the various components such as cable guides, motors, actuators, supports, buckles, and the like. The subject is fitted at S16 and calibration is performed at S18. The controller may be programmed at S20 with a prescribed treatment or exercise protocol. Data from the controller may be logged and prescriptions modified over a course of treatment or use as indicated at S22.

Figure 14A:
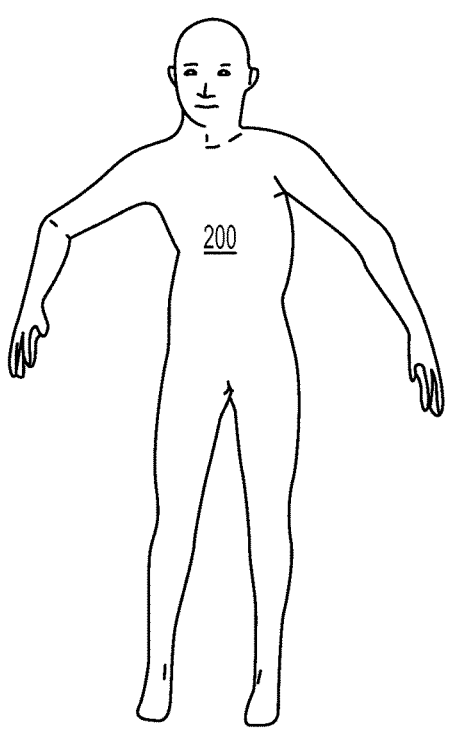
FIGS. 14A and 14B illustrate treatment of a musculoskeletal pathology using a virtual confinement field generated by the active brace, according to one or more embodiments of the disclosed subject matter.
Figure 14B:
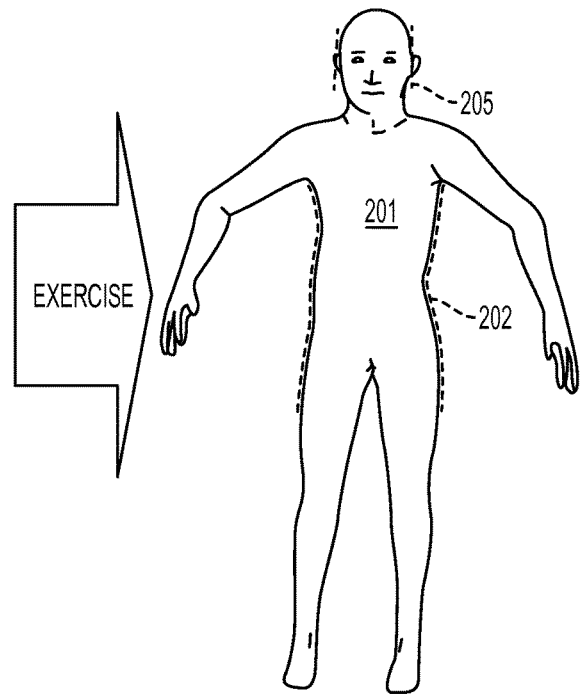
Figure 14C:
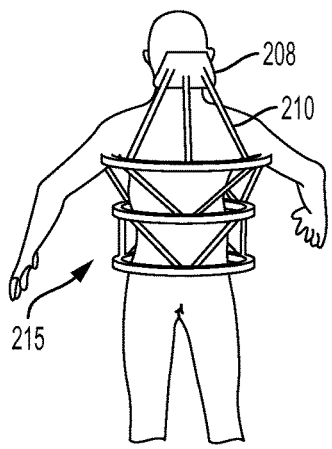
FIG. 14C shows an example of an actuated forcing or detecting element added to a brace, according to embodiments of the disclosed subject matter.

FIG. 13 shows a procedure for treating a musculoskeletal pathology, according to one or more embodiments of the disclosed subject matter. FIGS. 14A and 14B illustrate treatment of a musculoskeletal pathology using a virtual confinement field generated by the active brace, according to one or more embodiments of the disclosed subject matter. Referring to FIGS. 13, 14A and 14B, a subject 200 has a spinal deformity which according to a method is diagnosed at S50. At S52, a treatment plan is devised which may include the identification of muscles to be strengthened, flexibility to be developed, and mechanical manipulations to be effected on the spine. At S54, the subject is trained to use certain muscles to shift the spine in a desired way, which shifting may also strengthen muscles, and a brace is customized and fitted at S56. The shifting may stress targeted muscles, increase targeted flexibility, and/or mobilize joints of the spin and/or ribcage. The shifting may produce a target configuration that tightly fits a virtual conformation envelope 202 of the body 201 and head 205 as indicated in FIG. 14B. A brace configuration 215 in FIG. 14C may be used optionally with a head and/or neck adapter 208 that interfaces with the subject's head or neck. The head and/or neck adapter 208 may be fitted with sensors including pressure sensors. The brace structure 215 may include a support that is either flexible or pivoting to permit the head and/or neck adapter 208 to be moved by linear actuators 210. The head and/or neck adapter 208 may also be fixedly supported on a top ring. With the positioning of the pressure sensors adjacent the body, the controller is able to detect whether and to what degree the subject is able to effect and sustain the target configuration by detecting excess pressure thereby generating the virtual conformation envelope. The brace system may communicate with vibrational transducers to tell the subject when the target has been achieved and also to prompt the subject to rest or to achieve the target configuration. A prescription is created and programmed into the controller at S58 and S60, respectively. The controller may then implement the regimen according to the prescription S62. The processes of FIGS. 12 and 13 may be combined.

Note that although in most of the embodiments, the adapters that interface actuators with the body are ring shaped, it is possible to provide a similar or varied function by providing multiple pads, for example opposing sets of pads with a gap between, depending on the particular set of forces or motion constraint to be applied. In embodiments, a structural ring configuration such as rings 102, 103, and 104 in FIG. 1D or 1F may be provided, with shaping to accommodate shoulder blades, belly, upper arms and other features. Such rings may be larger than the subject in a set of fixed sizes and permit the attachment brace elements. The rings would be fitted with a variety of attachments for the actuators to permit customization in the location and number of actuators.

Figure 15:
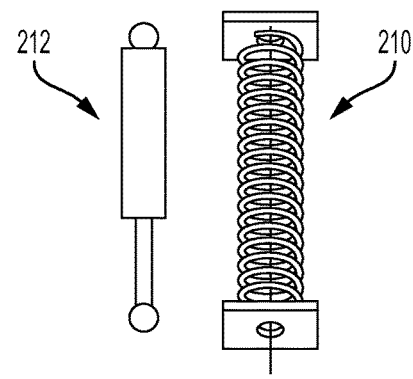
FIG. 15 shows alternative actuators for use in the active brace, according to embodiments of the disclosed subject matter.

As indicated, actuators can take a variety of forms. Passive devices such springs and elastic bands may be combined with actively controlled actuators. Referring to FIG. 15, cables (or driven belts) may be combined with compression-type springs for combinations 210 that behave equivalently, in essential respects, as linear actuators 212.

Various combinations of rigid links (with and without revolute or universal joints at their ends), and actuated interconnections of ring or other elements may be provided depending on the particular pathology or exercise requirement to be addressed.

According to first embodiments, the disclosed subject matter includes a mobile wearable body brace suitable for correcting a spinal deformity. At least three members are axially offset from and shaped to engage the trunk of a predefined person at different points along the caudal-cranial axis, the members being shaped, or configured to be able to shape, to conform closely with the trunk of the predefined person. One or more sensors are positioned on or between the at least three members and the trunk of the predefined person to provide real-time sensor data, the one or more sensors including pressure, shear, and/or temperature sensors. Actuators are selectively controlled by a controller and connecting one of the at least three members to another one of the at least three members, the number and placement of the actuators providing forces tending to displace, rotationally or linearly, at least one of the at least three members relative to another in a combination of multiple degrees of freedom. A programmable controller connected to the actuators controls the actuators and is programmed to generate the forces responsively to predefined parameters according to a treatment to be performed to correct the spinal deformity. A battery is sized to permit the self-sufficient powering of the actuators and the controller for autonomous and mobile use of the body brace.

Each first embodiment may be modified to form additional first embodiments in which the controller is programmed to generate the forces responsively to at least ones of the one or more sensors. Each first embodiment may be modified to form additional first embodiments in which the at least three members and the actuators are configured to lie close to the body such that a subject wearing the brace is able to walk and move about and such that normal arm swing motion is permitted when walking. Each first embodiment may be modified to form additional first embodiments in which the at least three is three and the three members form a stack with one inner and two outer ones, the outer ones being interconnected by adjustable fixed links and the inner one being able to move in three rotational modes and three displacement modes for a total of six degrees of freedom. Each first embodiment may be modified to form additional first embodiments in which the at least three is four and the three members form a stack with two inner and two outer ones, the inner ones being interconnected by adjustable fixed links and the outer ones being supported by the actuators as respective Stewart platforms and thus able to move in three rotational modes and three displacement modes for a total of six degrees of freedom. Each first embodiment may be modified to form additional first embodiments in which the at least three is three and the three members form a stack, two adjacent ones being interconnected by adjustable fixed links and the third being able to move in three rotational modes and three displacement modes for a total of six degrees of freedom.

Each first embodiment may be modified to form additional first embodiments in which at least some of the at least three members encircle the trunk. Each first embodiment may be modified to form additional first embodiments in which the at least three members are of rigid plastic. Each first embodiment may be modified to form additional first embodiments in which the actuators include in-line force transducers and the forces are generated responsively to signals from the force transducers. Each first embodiment may be modified to form additional first embodiments in which the controller is programmed to control selected ones of the actuators in a force mode in which they operate passively but maintain a selected force against forcing of one of the at least three members. Each first embodiment may be modified to form additional first embodiments that include a vibration transducer affixed to one of the at least three members and controlled by the controller as an output device to at least one of prompt the subject to take an action and provide feedback to the user based on signals from the sensors. Each first embodiment may be modified to form additional first embodiments wherein the controller contains a global positioning system (GPS) that indicates a geographical location of the subject, the controller being programmed to estimate an activity that the subject is engaged in at least in part in response the geographical location indicated by the GPS, the forces being generated at least in part responsively to the estimated activity. Each first embodiment may be modified to form additional first embodiments wherein the controller is programmed to generate the forces, at least in part, responsively to a time of day.

Each first embodiment may be modified to form additional first embodiments wherein the controller contains a transceiver that enables it to detect location by connecting with fixed transceivers such as an automobile Bluetooth transceiver or a home Wi-Fi network and the controller being programmed to estimate an activity that the subject is engaged in at least in part in response an indication of a connectable network indicated by the transceiver, the forces being generated at least in part responsively to the estimated activity. Each first embodiment may be modified to form additional first embodiments wherein the actuators are positioned and controlled such that a moment about the caudal-cranial axis is generated in at least one of the at least three members relative to at least another. Each first embodiment may be modified to form additional first embodiments wherein the actuators are positioned and controlled such that a moment about the anterior-posterior axis is generated in at least one of the at least three members relative to at least another thereby tending to cause a lateral bending force in the trunk of the subject.

Each first embodiment may be modified to form additional first embodiments wherein the actuators are positioned and controlled such that a moment about the transverse axis is generated in at least one of the at least three members relative to at least another thereby tending to cause a lordosis or kyphosis of the trunk of the subject. Each first embodiment may be modified to form additional first embodiments wherein the actuators are positioned and controlled such that a force along the caudal-cranial axis is generated in at least one of the at least three members relative to at least another thereby tending to create traction in the spine, either stretching or compressing the spine. Each first embodiment may be modified to form additional first embodiments that include shoulder straps. Each first embodiment may be modified to form additional first embodiments that include leg straps and shoulder straps to resist forces tending to cause two of the at least three members to move closer to each other, thereby compressing the trunk. Each first embodiment may be modified to form additional first embodiments that include leg straps.

Each first embodiment may be modified to form additional first embodiments that include a head and/or neck support attached to at least one of the three members. Each first embodiment may be modified to form additional first embodiments that include a head and/or neck support attached to at least one of the three members, the head and/or neck support including sensors positioned to lie adjacent the body of the subject. Each first embodiment may be modified to form additional first embodiments that include a head and/or neck support attached to at least one of the three members, the head and/or neck support including pressure sensors positioned to lie adjacent the body of the subject. Each first embodiment may be modified to form additional first embodiments that include a head and/or neck support with actuators to pivot the head and/or neck support anteriorly or posteriorly, the head and/or neck support being attached to at least one of the three members, the head and/or neck support including pressure sensors positioned to lie adjacent the body of the subject. Each first embodiment may be modified to form additional first embodiments that include a head and/or neck support with actuators to pivot the head and/or neck support anteriorly or posteriorly, the head and/or neck support being attached to at least one of the three members. Each first embodiment may be modified to form additional first embodiments that include a head and/or neck support with actuators to pivot the head and/or neck support in the coronal plane, the head and/or neck support being attached to at least one of the three members, the head and/or neck support including pressure sensors positioned to lie adjacent the body of the subject. Each first embodiment may be modified to form additional first embodiments that include a head and/or neck support with actuators to pivot the head and/or neck support in the coronal plane, the head and/or neck support being attached to at least one of the three members.

Each first embodiment may be modified to form additional first embodiments that include expandable bladders controlled by the controller and located between at least one of the at least three members to generate compression at points of the trunk. Each first embodiment may be modified to form additional first embodiments that include expandable bladders between at least one of the at least three members to provide a fit. Each first embodiment may be modified to form additional first embodiments that include expandable bladders controlled by the controller and located between at least one of the at least three members to improve fit. Each first embodiment can be modified to form additional first embodiments that include a speaker and speech synthesizer connected to the controller, the controller being programmed to announce the initiation of exercises including activation or changes in the actuators.

Each first embodiment may be modified to form additional first embodiments wherein the sensors include pressure sensors and further comprising vibrotactile transducers located at different positions on the brace, the controller being programmed to indicate a location of too much pressure or too little pressure according to a prescription at the respective position by generating a vibrotactile feedback at a respective one of the vibrotactile transducers. Each first embodiment may be modified to form additional first embodiments wherein at least one of the actuators includes cables and winches. Each first embodiment may be modified to form additional first embodiments wherein the actuators include cables and winches. Each first embodiment may be modified to form additional first embodiments wherein at least one of the actuators include cables and winches with springs positioned to resist the forces generated by tension in the cables. Each first embodiment may be modified to form additional first embodiments wherein the actuators include cables and winches with springs positioned to resist the forces generated by tension in the cables. Each first embodiment may be modified to form additional first embodiments wherein the controller is programmed to operate the actuators in force mode at first times and in position modes at second times.

Each first embodiment may be modified to form additional first embodiments that include the controller is programmed to operate the actuators in force mode at first times and in position modes at second times, wherein the times, a force of the force mode and positions of the position modes are determined according to a prescription stored in a data store and accessible to the controller. Each first embodiment may be modified to form additional first embodiments that include a visual display, the controller being programmed generating a visual feedback animation indicating a subject's degree of success responsively to the sensors. Each first embodiment may be modified to form additional first embodiments that include a user interface by which a subject can enter commands to the controller. Each first embodiment may be modified to form additional first embodiments that include a user interface by which a subject can enter commands to the controller wherein the commands are enabled according to a prescription stored on a data store and accessible to the controller. Each first embodiment may be modified to form additional first embodiments that include the one or more sensors include pressure sensors, temperature sensors, and motion sensors.

Each first embodiment may be modified to form additional first embodiments that include the actuators include position encoders and the controller is programmed to calculate a trunk configuration from displacements of the actuators. Each first embodiment may be modified to form additional first embodiments that include the sensor data includes pressure, temperature, motion, and joint angle data. Each first embodiment may be modified to form additional first embodiments that include the actuators and the at least three members and actuators are interconnected as a Stewart-platform. Each first embodiment may be modified to form additional first embodiments that include the actuators are linear actuators and the combination of the at least three members and the actuators form a Stewart-platform. Each first embodiment may be modified to form additional first embodiments that include the actuators are linear actuators and their number and placement is such that forces tending to rotate at least one outer member relative to the middle member may be selectively generated by the controller. Each first embodiment may be modified to form additional first embodiments that include the actuators are linear actuators and their number and placement is such that forces tending to mutually axially displace at least one outer member relative to the middle member may be selectively generated by the controller. Each first embodiment may be modified to form additional first embodiments that include the actuators are linear actuators and their number and placement is such that forces tending to rotate at least one outer member relative to the middle member and forces tending to mutually axially displace at least one outer member relative to the middle member may be selectively generated by the controller.

Each first embodiment may be modified to form additional first embodiments that include the controller is programmed to modulate forces applied by the brace to generate continuous and oscillatory motion of spine. Each first embodiment may be modified to form additional first embodiments wherein the controller is programmed to modulate forces applied by the brace to generate continuous and massaging of the muscles. Each first embodiment may be modified to form additional first embodiments wherein the controller is programmed to temporarily generate a force calculated to induce a reflex. Each first embodiment may be modified to form additional first embodiments wherein the controller is programmed to temporarily generate a force calculated to induce a reflex and further programmed to detect pressure signals in response to an induced reflex. Each first embodiment may be modified to form additional first embodiments wherein the controller is programmed to generate a log responsively to data from the sensors.

The disclosed embodiments include a method of using any of the brace embodiments. The method includes fitting the at least three members to the torso of a scoliosis patient, providing a prescription and/or individual profile information into the controller corresponding to the anatomical configuration of the patient, and using the controller, applying corrective forces through the at least three members to the patient's torso.

According to embodiments, the disclosed subject matter includes a wearable brace mechanism for dynamically modulating corrective forces along a natural curve of the spine of a person and responding to the effects of the brace on the spine as it adjusts over time. At least three orthosis elements conform to the torso of a predefined person, each orthosis element being disposed being positioned at a different axial part of the torso. A plurality of sensors are positioned between the rings and the upper torso to capture sensor data relating to one or more of a pressure, temperature, motion, and/or joint angle. One or more closed-loop-controlled actuators attach to adjacent rings to apply a force on each of the orthosis elements responsively to the sensor data received by the controller.

The disclosed embodiments include a method for dynamically modulating corrective forces along a natural curve of the spine of a person and responding to the effects of the brace on the spine as it adjusts over time. The method includes measuring one or more of pressure, temperature, motion, and/or joint angle using a plurality of sensors positioned between a series rings snugly attached to the torso of a user to conform to different cross-sections in the upper torso, and the upper torso. The method further includes actuating one or more actuators, each of which connects a middle ring to an outer ring in the series, to apply a force onto each of the rings based on the sensor data received. In the method, the forces applied are dynamically changed over time.

According to second embodiments, the disclosed subject matter includes a system for correcting a curve in a body part. A plurality of ring-like elements connects to each other and attach to the body part at different cross-sections. One or more sensors are positioned between the plurality of ring-like elements and the body part to provide real-time sensor data. One or more actuators attached to adjacent ring-like elements to provide forces to the plurality of elements based on the sensor data received from the one or more sensors. Forces to be applied to the plurality of elements from the actuators are dynamically modulated based on the body part geometry and the received sensor data. The second embodiments can be modified to form additional second embodiments in which the one or more sensors include pressure sensors, temperature sensors, and motion sensors. The second embodiments can be modified to form additional second embodiments in which the sensor data includes pressure, temperature, motion, and joint angle data. The second embodiments can be modified to form additional second embodiments in which the ring-like elements are actuated using one of a cable-driven, Stewart-platform, or a compliant mechanism.

According to third embodiments, the disclosed subject matter includes a wearable brace mechanism for dynamically modulating corrective forces along a natural curve of the spine of a person and respond to the effects of the brace on the spine as it adjusts over time. A series of rings snugly attach to the torso of a user to conform to different cross-sections in the upper torso. A plurality of sensors are positioned between the rings and the upper torso to capture sensor data relating to one or more of a pressure, temperature, motion, and/or joint angle. One or more closed-loop actuators are attached to adjacent rings to apply a forces on each of the rings based on the sensor data received.

According to fourth embodiments, the disclosed subject matter includes a method for dynamically modulating corrective forces along a natural curve of the spine of a person and respond to the effects of the brace on the spine as it adjusts over time. The method includes measuring one or more of pressure, temperature, motion, and/or joint angle using a plurality of sensors positioned between a series rings snugly attached to the torso of a user to conform to different cross-sections in the upper torso, and the upper torso. The method further includes actuating a plurality of actuators attached to each adjacent ring to apply a force onto each of the rings based on the sensor data received, wherein the forces applied are dynamically changed over time.

According to fifth embodiments, the disclosed subject matter includes a body brace with at least three members axially offset from and shaped to engage the trunk of a predefined person at different points along the caudal-cranial axis. The members are shaped, or configured to be able to shape, to conform closely with the trunk of the predefined person. Actuators are selectively controlled by a controller and connecting one of the at least three members to another one of the at least three members, the number and placement of the actuators providing forces tending to displace, rotationally or linearly, at least one of the at least three members relative to another in a combination of multiple degrees of freedom. A programmable controller connects to the actuators to control them and programmed to generate the forces responsively to predefined parameters according to a predefined prescription stored in a data store accessible to the controller. The fifth embodiments can be modified to form additional fifth embodiments that include one or more sensors positioned on or between the at least three members and the trunk of the predefined person to provide real-time sensor data, the one or more sensors including pressure, shear, and/or temperature sensors.

The fifth embodiments can be modified to form additional fifth embodiments in which the controller is programmed to generate the forces responsively to at least ones of the one or more sensors. The fifth embodiments can be modified to form additional fifth embodiments in which the at least three members and the actuators are configured to lie close to the body such that a subject wearing the brace is able to walk and move about and such that normal arm swing motion is permitted when walking. The fifth embodiments can be modified to form additional fifth embodiments in which the at least three is three and the three members form a stack with one inner and two outer ones, the outer ones being interconnected by adjustable fixed links and the inner one being able to move in three rotational modes and three displacement modes for a total of six degrees of freedom. The fifth embodiments can be modified to form additional fifth embodiments in which the at least three is four and the three members form a stack with two inner and two outer ones, the inner ones being interconnected by adjustable fixed links and the outer ones being supported by the actuators as respective Stewart platforms and thus able to move in three rotational modes and three displacement modes for a total of six degrees of freedom.

The fifth embodiments can be modified to form additional fifth embodiments in which the at least three is three and the three members form a stack, two adjacent ones being interconnected by adjustable fixed links and the third being able to move in three rotational modes and three displacement modes for a total of six degrees of freedom. The fifth embodiments can be modified to form additional fifth embodiments in which at least some of the at least three members encircle the trunk. The fifth embodiments can be modified to form additional fifth embodiments in which the at least three members are of rigid plastic. The fifth embodiments can be modified to form additional fifth embodiments in which the actuators include in-line force transducers and the forces are generated responsively to signals from the force transducers. The fifth embodiments can be modified to form additional fifth embodiments in which the controller is programmed to control selected ones of the actuators in a force mode in which they operate passively but maintain a selected force against forcing of one of the at least three members. The fifth embodiments can be modified to form additional fifth embodiments that include a vibration transducer affixed to one of the at least three members and controlled by the controller as an output device to at least one of prompt the subject to take an action and provide feedback to the user based on signals from the sensors.

The fifth embodiments can be modified to form additional fifth embodiments in which the controller contains a global positioning system (GPS) that indicates a geographical location of the subject, the controller being programmed to estimate an activity that the subject is engaged in at least in part in response the geographical location indicated by the GPS, the forces being generated at least in part responsively to the estimated activity. The fifth embodiments can be modified to form additional fifth embodiments in which the controller is programmed to generate the forces, at least in part, responsively to a time of day. The fifth embodiments can be modified to form additional fifth embodiments in which the controller contains a transceiver that enables it to detect location by connecting with fixed transceivers such as an automobile Bluetooth transceiver or a home Wi-Fi network and the controller being programmed to estimate an activity that the subject is engaged in at least in part in response an indication of a connectable network indicated by the transceiver, the forces being generated at least in part responsively to the estimated activity.

The fifth embodiments can be modified to form additional fifth embodiments in which the actuators are positioned and controlled such that a moment about the caudal-cranial axis is generated in at least one of the at least three members relative to at least another. The fifth embodiments can be modified to form additional fifth embodiments in which the actuators are positioned and controlled such that a moment about the anterior-posterior axis is generated in at least one of the at least three members relative to at least another thereby tending to cause a lateral bending force in the trunk of the subject. The fifth embodiments can be modified to form additional fifth embodiments in which the actuators are positioned and controlled such that a moment about the transverse axis is generated in at least one of the at least three members relative to at least another thereby tending to cause a lordosis or kyphosis of the trunk of the subject. The fifth embodiments can be modified to form additional fifth embodiments in which the actuators are positioned and controlled such that a force along the caudal-cranial axis is generated in at least one of the at least three members relative to at least another thereby tending to create traction in the spine, either stretching or compressing the spine.

The fifth embodiments can be modified to form additional fifth embodiments that include shoulder straps. The fifth embodiments can be modified to form additional fifth embodiments that include leg straps and shoulder straps to resist forces tending to cause two of the at least three members to move closer to each other, thereby compressing the trunk. The fifth embodiments can be modified to form additional fifth embodiments that include leg straps. The fifth embodiments can be modified to form additional fifth embodiments that include a head and/or neck support attached to at least one of the three members. The fifth embodiments can be modified to form additional fifth embodiments that include a head and/or neck support attached to at least one of the three members, the head and/or neck support including sensors positioned to lie adjacent the body of the subject. The fifth embodiments can be modified to form additional fifth embodiments that include a head and/or neck support attached to at least one of the three members, the head and/or neck support including pressure sensors positioned to lie adjacent the body of the subject.

The fifth embodiments can be modified to form additional fifth embodiments that include a head and/or neck support with actuators to pivot the head and/or neck support anteriorly or posteriorly, the head and/or neck support being attached to at least one of the three members, the head and/or neck support including pressure sensors positioned to lie adjacent the body of the subject. The fifth embodiments can be modified to form additional fifth embodiments that include a head and/or neck support with actuators to pivot the head and/or neck support anteriorly or posteriorly, the head and/or neck support being attached to at least one of the three members. The fifth embodiments can be modified to form additional fifth embodiments that include a head and/or neck support with actuators to pivot the head and/or neck support in the coronal plane, the head and/or neck support being attached to at least one of the three members, the head and/or neck support including pressure sensors positioned to lie adjacent the body of the subject. The fifth embodiments can be modified to form additional fifth embodiments that include a head and/or neck support with actuators to pivot the head and/or neck support in the coronal plane, the head and/or neck support being attached to at least one of the three members. The fifth embodiments can be modified to form additional fifth embodiments that include expandable bladders controlled by the controller and located between at least one of the at least three members to generate compression at points of the trunk.

The fifth embodiments can be modified to form additional fifth embodiments that include expandable bladders between at least one of the at least three members to provide a fit. The fifth embodiments can be modified to form additional fifth embodiments that include expandable bladders controlled by the controller and located between at least one of the at least three members to improve fit. The brace of claim 66, with a speaker and speech synthesizer connected to the controller, the controller being programmed to announce the initiation of exercises including activation or changes in the actuators. The fifth embodiments can be modified to form additional fifth embodiments in which the sensors include pressure sensors and further comprising vibrotactile transducers located at different positions on the brace, the controller being programmed to indicate a location of too much pressure or too little pressure according to a prescription at the respective position by generating a vibrotactile feedback at a respective one of the vibrotactile transducers. The fifth embodiments can be modified to form additional fifth embodiments in which at least one of the actuators includes cables and winches. The fifth embodiments can be modified to form additional fifth embodiments in which the actuators include cables and winches. The fifth embodiments can be modified to form additional fifth embodiments in which at least one of the actuators include cables and winches with springs positioned to resist the forces generated by tension in the cables.

The fifth embodiments can be modified to form additional fifth embodiments in which the actuators include cables and winches with springs positioned to resist the forces generated by tension in the cables. The fifth embodiments can be modified to form additional fifth embodiments in which the controller is programmed to operate the actuators in force mode at first times and in position modes at second times. The fifth embodiments can be modified to form additional fifth embodiments in which the controller is programmed to operate the actuators in force mode at first times and in position modes at second times, wherein the times, a force of the force mode and positions of the position modes are determined according to a prescription stored in a data store and accessible to the controller. The fifth embodiments can be modified to form additional fifth embodiments that include a visual display, the controller being programmed generating a visual feedback animation indicating a subject's degree of success responsively to the sensors. The fifth embodiments can be modified to form additional fifth embodiments that include a user interface by which a subject can enter commands to the controller. The fifth embodiments can be modified to form additional fifth embodiments that include a user interface by which a subject can enter commands to the controller wherein the commands are enabled according to a prescription stored on a data store and accessible to the controller.

The fifth embodiments can be modified to form additional fifth embodiments in which the one or more sensors include pressure sensors, temperature sensors, and motion sensors. The fifth embodiments can be modified to form additional fifth embodiments in which the actuators include position encoders and the controller is programmed to calculate a trunk configuration from displacements of the actuators. The fifth embodiments can be modified to form additional fifth embodiments in which the sensor data includes pressure, temperature, motion, and joint angle data. The fifth embodiments can be modified to form additional fifth embodiments in which the actuators and the at least three members and actuators are interconnected as a Stewart-platform. The fifth embodiments can be modified to form additional fifth embodiments in which the actuators are linear actuators and the combination of the at least three members and the actuators form a Stewart-platform. The fifth embodiments can be modified to form additional fifth embodiments in which the actuators are linear actuators and their number and placement is such that forces tending to rotate at least one outer member relative to the middle member may be selectively generated by the controller. The fifth embodiments can be modified to form additional fifth embodiments in which the actuators are linear actuators and their number and placement is such that forces tending to mutually axially displace at least one outer member relative to the middle member may be selectively generated by the controller.

The fifth embodiments can be modified to form additional fifth embodiments in which the actuators are linear actuators and their number and placement is such that forces tending to rotate at least one outer member relative to the middle member and forces tending to mutually axially displace at least one outer member relative to the middle member may be selectively generated by the controller. The fifth embodiments can be modified to form additional fifth embodiments in which the controller is programmed to modulate forces applied by the brace to generate continuous and oscillatory motion of spine. The fifth embodiments can be modified to form additional fifth embodiments in which the controller is programmed to modulate forces applied by the brace to generate continuous and massaging of the muscles. The fifth embodiments can be modified to form additional fifth embodiments in which the controller is programmed to temporarily generate a force calculated to induce a reflex. The fifth embodiments can be modified to form additional fifth embodiments in which the controller is programmed to temporarily generate a force calculated to induce a reflex and further programmed to detect pressure signals in response to an induced reflex. The fifth embodiments can be modified to form additional fifth embodiments in which the controller is programmed to generate a log responsively to data from the sensors.

According to sixth embodiments, the disclosed subject matter includes a dynamic wearable brace for active control of a user's body. The brace can comprise at least three members axially offset from and shaped to engage respective portions of the user's body. The brace can further include one or more sensors that provide signals indicative of at least one of pressure, shear, and/or temperature. The brace can further include a plurality of actuators, each of which connects between two of the axially offset members. The actuators being configured to provide forces tending to displace at least one of the axially offset members with respect to another of the axially offset members. The brace can further include a controller to control the plurality of actuators to generate active control of the user's body and/or responsively to signals from said one or more sensors.

The sixth embodiments can be modified to form additional sixth embodiments in which the controller is programmed to generate forces responsively to signals from said one or more sensors. The sixth embodiments can be modified to form additional sixth embodiments in which at least one of the actuators is a cable and winch or a linear actuator. The sixth embodiments can be modified to form additional sixth embodiments in which the axially offset members and the actuators are interconnected as one or more Stewart platforms. The sixth embodiments can be modified to form additional sixth embodiments in which a method of using the brace comprises fitting the axially offset members to the torso of the user who has scoliosis, and controlling the actuators to apply forces to the user to treat said scoliosis. The sixth embodiments can be modified to form additional sixth embodiments in which a method of using the brace comprises fitting the axially offset members to the torso of the user, and controlling the actuators to apply forces to the user to exercise particular muscles of the user.

It will be appreciated that the disclosed modules, processes, or systems associated with control or use of the spinal treatment/adjustment device may be implemented in hardware, hardware programmed by software, software instruction stored on a non-transitory computer readable medium or a combination of the above. For example, any of the methods or processes disclosed herein may be implemented, for example, using a processor configured to execute a sequence of programmed instructions stored on a non-transitory computer readable medium, which processor and/or computer readable medium may be part of a system configured to control or use of the spinal adjustment device. For example, the processor can include, but is not limited to, a personal computer or workstation or other such computing system that includes a processor, microprocessor, microcontroller device, or is comprised of control logic including integrated circuits such as, for example, an Application Specific Integrated Circuit (ASIC). The instructions may be compiled from source code instructions provided in accordance with a programming language such as Java, C++, C#.net or the like. The instructions can also comprise code and data objects provided in accordance with, for example, the Visual Basic™ language, Lab VIEW, or another structured or object-oriented programming language. The sequence of programmed instructions and data associated therewith may be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, any of the methods or processes disclosed herein may be implemented as a single processor or as a distributed processor, which single or distributed processor may be part of a system configured to control or use the spinal treatment/adjustment device. Further, it should be appreciated that the steps mentioned herein may be performed on a single or distributed processor (single and/or multi-core). Also, any of the methods or processes described in the various figures of and for embodiments herein may be distributed across multiple computers or systems or may be co-located in a single processor or system. Exemplary structural embodiment alternatives suitable for implementing any of the methods or processes described herein are provided below.

Any of the methods or processes described above may be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example, any of which may be part of a system configured to control or use the spinal treatment/adjustment device.

Embodiments of the methods, processes, and systems (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein may be used to implement embodiments of the methods, systems, or computer program products (i.e., software program stored on a non-transitory computer readable medium).

Furthermore, embodiments of the disclosed methods, processes, or systems may be readily implemented, fully or partially, in software using, for example, object or object-oriented software development environments that provide portable source code that may be used on a variety of computer platforms. Alternatively, embodiments of the disclosed methods, processes, or systems may be implemented partially or fully in hardware using, for example, standard logic circuits or a very-large-scale integration (VLSI) design. Other hardware or software may be used to implement embodiments depending on the speed and/or efficiency requirements of the systems, the particular function, and/or particular software or hardware system, microprocessor, or microcomputer being utilized. Embodiments of the disclosed methods, processes, or systems may be implemented in hardware and/or software using any known or later developed systems or structures, devices and/or software by those of ordinary skill in the art from the function description provided herein and with knowledge of computer programming arts.

Furthermore, the foregoing descriptions apply, in some cases, to examples generated in a laboratory, but these examples may be extended to production techniques. For example, where quantities and techniques apply to the laboratory examples, they should not be understood as limiting. In addition, although specific materials have been disclosed herein, other materials may also be employed according to one or more contemplated embodiments.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, system, methods, and devices for scoliosis correction and/or spinal adjustment. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicant intends to embrace all such alternatives, modifications, equivalents, and variations that are within the spirit and scope of the present invention.

The invention claimed is:

1. A mobile wearable body brace suitable for correcting a spinal deformity of a person, comprising:
   at least three members axially offset from each other and shaped to engage a trunk of the person at different points along the caudal-cranial axis, the members being shaped, or configured to be able to shape, to conform closely with the trunk of the person;
   one or more sensors positioned on or between the at least three members and the trunk of the person to provide real-time sensor data, the one or more sensors including pressure, shear, and/or temperature sensors;
   actuators selectively controlled by a controller and connecting one of the at least three members to another one of the at least three members, the number and placement of the actuators providing forces tending to displace, rotationally or linearly, at least one of the at least three members relative to another in a combination of multiple degrees of freedom, wherein one of the at least three members is able to move in three rotational modes and three displacement modes for a total of six degrees of freedom relative to another of the at least three members;
   the controller connected to the actuators to control them, wherein the controller is a programmable controller programmed to generate said forces responsively to predefined parameters according to a treatment to be performed to correct the spinal deformity; and
   a battery sized to permit self-sufficient powering of said actuators and said controller for autonomous and mobile use of said body brace.

2. The brace of claim 1, wherein the controller is programmed to generate said forces responsively to at least ones of the one or more sensors.

3. The brace of claim 1, wherein the at least three members and the actuators are configured to lie close to the body of the person such that the person wearing the brace is able to walk and move about and such that normal arm swing motion is permitted when walking.

4. The brace of claim 1, wherein the at least three members is three members and the three members form a stack with one inner member and two outer members, the outer members being interconnected by adjustable fixed links.

5. The brace of claim 1, wherein the at least three members is four members and the four members form a stack with two inner and two outer ones of the members, the inner ones of the four members being interconnected by adjustable fixed links and the outer ones of the four members being supported by the actuators as respective Stewart platforms and thus able to move in three rotational modes and three displacement modes for a total of the six degrees of freedom.

6. The brace of claim 1, wherein the at least three members is three members and the three members form a stack, two adjacent ones of the members being interconnected by adjustable fixed links and a third one of the members being able to move in three rotational modes and three displacement modes for a total of the six degrees of freedom.

7. The brace of claim 1, wherein at least some of the at least three members encircle the trunk.

8. The brace of claim 1, wherein the at least three members are of rigid plastic.

9. The brace of claim 1, wherein the actuators include in-line force transducers and the forces are generated responsively to signals from the in-line force transducers.

10. The brace of claim 1, wherein the controller is programmed to control selected ones of the actuators in a force mode in which they operate passively but maintain a selected force against forcing of one of said at least three members.

11. The brace of claim 1, further comprising a vibration transducer affixed to one of said at least three members and controlled by the controller as an output device to at least one of prompt the person to take an action and provide feedback to the person based on signals from the sensors.

12. The brace of claim 1, wherein the controller is programmed to generate said forces, at least in part, responsively to a time of day.

13. The brace of claim 1, wherein the controller contains a transceiver that enables it to detect location by connecting with fixed transceivers and the controller being programmed to estimate an activity that the person is engaged in at least in part in response to an indication of a connectable network indicated by the transceiver, said forces being generated at least in part responsively to the estimated activity.

14. The brace of claim 1, wherein the actuators are positioned and controlled such that a moment about the caudal-cranial axis is generated in at least one of the at least three members relative to at least another.

15. The brace of claim 1, wherein the actuators are positioned and controlled such that a moment about the anterior-posterior axis is generated in at least one of the at least three members relative to at least another thereby tending to cause a lateral bending force in the trunk of the person.

16. The brace of claim 1, wherein the actuators are positioned and controlled such that a moment about the transverse axis is generated in at least one of the at least three members relative to at least another thereby tending to cause a lordosis or kyphosis of the trunk of the person.

17. The brace of claim 1, wherein the actuators are positioned and controlled such that a force along the caudal-cranial axis is generated in at least one of the at least three members relative to at least another thereby tending to create traction in the spine, either stretching or compressing the spine.

18. The brace of claim 1, further comprising a head and/or neck support attached to at least one of the three members.

19. The brace of claim 1, further comprising a head and/or neck support attached to at least one of the three members, the head and/or neck support including sensors positioned to lie adjacent the body of the person.

20. The brace of claim 1, further comprising a head and/or neck support attached to at least one of the three members, the head and/or neck support including pressure sensors positioned to lie adjacent the body of the person.

21. The brace of claim 1, further comprising a head and/or neck support with actuators to pivot the head and/or neck support anteriorly or posteriorly, the head and/or neck support being attached to at least one of the three members, the head and/or neck support including pressure sensors positioned to lie adjacent the body of the person.

22. The brace of claim 1, further comprising a head and/or neck support with actuators to pivot the head and/or neck support in the coronal plane, the head and/or neck support being attached to at least one of the three members, the head and/or neck support including pressure sensors positioned to lie adjacent the body of the person.

23. The brace of claim 1, wherein the sensors include pressure sensors and further comprising vibrotactile transducers located at different positions on the brace, the controller being programmed to indicate a location of too much pressure or too little pressure according to a prescription at a respective position by generating a vibrotactile feedback at a respective one of the vibrotactile transducers.

* * * * *